(12) United States Patent
Amjad et al.

(10) Patent No.: US 8,789,530 B2
(45) Date of Patent: Jul. 29, 2014

(54) CLOSED LOOP RESPIRATORY SUPPORT DEVICE WITH DYNAMIC ADAPTABILITY

(75) Inventors: Ramak Amjad, McAllen, TX (US); Roger Fales, Columbia, MO (US); Timothy Keim, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 544 days.

(21) Appl. No.: 13/116,841

(22) Filed: May 26, 2011

(65) Prior Publication Data

US 2011/0290252 A1    Dec. 1, 2011

Related U.S. Application Data

(60) Provisional application No. 61/396,385, filed on May 26, 2010.

(51) Int. Cl.
*A61M 11/00* (2006.01)

(52) U.S. Cl.
USPC .............................. 128/204.23; 128/204.21

(58) Field of Classification Search
USPC ........... 128/204.18–204.23, 205.11, 920, 923
See application file for complete search history.

(56) References Cited

U.S. PATENT DOCUMENTS

| 4,121,578 A | 10/1978 | Torzala |
| 5,991,525 A | 11/1999 | Shah et al. |
| 6,532,958 B1 | 3/2003 | Buan et al. |
| 6,761,165 B2 * | 7/2004 | Strickland, Jr. .......... 128/204.22 |
| 2003/0189492 A1 | 10/2003 | Harvie |
| 2011/0290252 A1 * | 12/2011 | Amjad et al. ............. 128/204.23 |
| 2012/0000462 A1 * | 1/2012 | Edwards et al. ......... 128/201.21 |

* cited by examiner

*Primary Examiner* — Steven Douglas
(74) *Attorney, Agent, or Firm* — Polsinelli PC

(57) ABSTRACT

The disclosure provides an automatic system based on the dynamic adaptability strategy for controlling oxygen concentration in blood of patients with fluctuating oxygen needs. The system monitors patient's clinical measurement data and updates the system continuously, which provides changes in $FiO_2$ and gas flow that are more patient specific and reduce the patient's unnecessary oxygen exposure.

17 Claims, 54 Drawing Sheets
(45 of 54 Drawing Sheet(s) Filed in Color)

CLOSED LOOP RESPIRATORY SUPPORT DEVICE WITH DYNAMIC ADAPTABILITY

CROSS REFERENCE TO RELATED APPLICATION

This application claims priority from U.S. Provisional Application Ser. No. 61/396,385, filed on May 26, 2010, which is hereby incorporated by reference in its entirety.

FIELD OF THE INVENTION

The present invention relates to a novel control system designed to automatically control arterial oxygen saturation in a patient with fluctuating oxygen needs, such as a premature infant, sleep apnea patient, any patient on respiratory support device, and any person or animal on a respiratory support device. In particular, the system is comprised of a mechatronic device that is designed to automatically sense the oxygen saturation ($SpO_2$) in a patient's blood and fraction of inspired oxygen ($FiO_2$) being delivered to the patient and independently adjust the flow of gas and percentage of oxygen delivered to the patient as required to achieve the set $SpO_2$ parameters. The invention additionally provides stimulation in the event of an apnea event.

The system additionally comprises a method for automatically monitoring and controlling fluctuating oxygen saturation in the blood of a patient using the device combined with an adaptive aspect such that the system operates automatically in the presence of varying parameters that describe the patient's dynamic response characteristics given the differences between patients. The parameters are not known due to the differences between patients. In particular, the method is adaptable to a variety of patients and provides precise control of $SpO_2$ due to the incorporation of a novel estimation system. The estimation system estimates and determines unknown disturbances, which cause desaturation events in the patient, and varying parameters as between patients upon receipt of signals obtained from monitoring devices connected to sensors applied to the patient.

BACKGROUND OF THE INVENTION

One of the most common respiratory problems found in premature infants is Respiratory Distress Syndrome (RDS). RDS is caused by a deficiency in pulmonary surfactant production in neonates with a low level of lung maturity. Treatment for RDS and subsequent chronic lung disease involves placing the infant on a respiratory support device such as a respirator or ventilator, giving exogenous surfactant, and supporting the infant until the lungs mature. Another problem common in premature infants is retinopathy of prematurity (ROP). ROP is partially caused by high oxygen saturation coupled with large fluctuations in $FiO_2$ delivered to the infant. ROP is a leading cause of blindness and visual impairment in premature neonates and is due in part to the effects of oxygen on the developing blood vessels of the infant's retina.

To help prevent the occurrence of ROP in a premature infant, the arterial oxygen saturation ($SpO_2$) should be maintained within a certain range, usually 85%-92%. Alarms are set in the clinical setting to notify medical professionals if the premature infant's $SpO_2$ level falls outside the prescribed range. In the event the $SpO_2$ falls below 85%, a state of hypoxia could result in tissue damage in brain injury. If the $SpO_2$ level rises above 92%, a state of hyperoxia could result in an increased risk for ROP which could result in visual impairment, even blindness.

With regard to infants, apnea is the cessasation of pulmonary air flow usually for 20 seconds or more. Apnea of prematurity is observed in more than half of surviving premature infants born at less than 30 weeks gestation. Because of the periods of apnea and chronic lung disease, the $SpO_2$ can decline outside of the prescribed range. This period of decline in $SpO_2$ is called a desaturation period. If the apnea event is present and prolonged, the infant will have a desaturation which then results in a drop in heart rate called a bradycardia. These continuous cycles of apnea, desaturation, and bradycardia (referred to in the medical field as ABD's) can cause long term neurologic problems. The treatment to avoid these neurologic problems involves increasing the $FiO_2$ during the ABD and stimulating the infant to breathe. The fluctuations in $FiO_2$ to treat ABD's increase the risk for ROP. Maintaining a constant $FiO_2$ level by keeping the fluctuations to a minimum, as well limiting the time on higher $FiO_2$, have been shown to decrease the incidence of ROP.

$SpO_2$ is measured in a patient using a noninvasive pulse oximeter and is regulated by adjusting the fraction of inspired oxygen ($FiO_2$) and the flow of the delivered gas. Currently, medical professionals manually adjust the $FiO_2$ and flow based on medical practice and their best judgment. Specifically, a medical professional will turn a blend valve knob to adjust $FiO_2$ settings. The flow of gas to the patient is manually set to a preset amount and is typically not changed without a physician's order. When a desaturation event occurs, the medical professional will increase the oxygen level by adjusting the blend valve to aid in the recovery from the event. A typical response to apnea is to use tactile simulation to remind the premature infant to begin breathing again.

However, human intervention may be time consuming, expensive, and problematic at times. For instance, medical professionals tend to have heavy workloads and are usually tasked with taking care of more than one patient at a time. Due to this workload, the patient does not always receive the interventions that are necessary to aid in recovery or the interventions are delayed. Additionally, the patients are typically observed by a rotation of medical professionals during any given period of time. Rotational supervision of the premature infant's $SpO_2$ combined with manual judgment-based adjustment of $FiO_2$ can result in inconsistent treatment to the infant, possibly hindering the infant's recovery.

Because the ABD cycle can be harmful to premature infants and the workload of medical professionals is oftentimes demanding, there is a need in the art for a system that can automatically adjust $FiO_2$ measurements based on fluctuating $SpO_2$ without the need for manual adjustment of $FiO_2$ and flow of delivered gas. A need exists in the art for a system that provides real time or close to real time adjustments to $FiO_2$ levels to aid in providing a constant $FiO_2$ and $SpO_2$ level in the patient. While a number of automatic control systems for the ventilation of premature infants have been discussed in the prior art, none incorporate an adaptive aspect such that they can operate in the presence of varying parameters as a result of differences among patients. Accordingly, there is a need in the art for a automatic control system having dynamic adaptability such that the level of care provided to the patient by medical professionals is maintained while the number of manual interventions is reduced.

SUMMARY OF THE INVENTION

The invention provides for an automatic system for controlling $SpO_2$ in the blood of any patient placed on respiratory support, as well as a device for providing stimulation in patients having apnea. The system of the present invention also has application to other gas control systems besides oxygen control systems. The invention further relates to a method for controlling SpO$_2$ in the blood of patients. The inventive system monitors a patient's clinical measurements (e.g., FiO$_2$, SpO$_2$, and vital signs such as heart rate, blood pressure, and respiration rate) and updates a patient-specific adaptive model continuously at a pre-determined interval based on a dynamic adaptability strategy.

The system of the present invention automatically monitors and controls the oxygen content of a patient's blood. The system generally includes a monitoring device, a microcontroller, a device for controlling FiO$_2$, and a device for providing dynamic adaptability of the system, Specifically, the system of the present invention comprises a microcontroller, a monitoring device, a device for variable adjustment of FiO$_2$ using a blend valve, and a device for providing dynamic adaptability of the system. Additionally, the system may further comprise a device for variable adjustment of flow of delivered gas to a patient using a flow valve and/or a device for stimulating the patient as reminders to breathe. The microcontroller receives signals pertaining to the patient's clinical measurements obtained from the monitoring device. Depending on the input received, the microcontroller dynamically adapts its control algorithm based on the current input and historical input obtained from the patient. Once the input has been analyzed and processed, the microcontroller sends signals to the device controlling FiO$_2$. The microcontroller may additionally send signals to a device controlling flow of gas to the patient. Additionally, a device for stimulating the patient may be attached to an extremity of the patient (e.g., toe, foot, finger, or wrist) to simulate tactile stimulation that normally is provided manually by the medical professional to stimulate/remind the patient to breathe during an apnea event.

The present invention also provides for a method of using the system as described. The method comprises the steps of (1) monitoring a patient that has been placed on respiratory support, (2) sensing the FiO$_2$ and SpO$_2$ of the patient at either pre-determined intervals, in a continuous manner, or combinations thereof, (3) determining with dynamic adaptability through algorithm the required voltage to send to a device variably adjusting FiO$_2$ through a blend valve, and (4) automatically adjusting the blend valve to provide optimum FiO$_2$ as required by the patient. Optionally, the method may additionally or alternatively comprise the steps of determining through algorithm the required voltage to send to a device variably adjusting the flow of gas through a flow valve, and automatically adjusting the flow valve to provide the optimum flow output required by the patient.

The present invention further provides for a method of automatically monitoring, adjusting, and controlling fluctuating SpO$_2$ in the blood of patients using the system described (or portions thereof). The method enables the system of the present invention to possess dynamic adaptability, which is a novel feature of the inventive system. Based on the signal received by the microcontroller from the monitoring device, an adaptive controller can determine the optimal FiO$_2$ input to maintain the prescribed SpO$_2$ for the patient. The adaptive controller is based on a learning algorithm (i.e., dynamic adaptability), which is designed to improve performance of the system on a specific patient the longer the system is used on that given patient. The combined features of the system of the present invention account for breathing patterns, heart rate and oxygen saturation, and adjust the flow of gas and delivered FiO$_2$ to the patient accordingly. The system of the present invention is designed to simulate the level of care that patients on respiratory support, especially premature infants, traditionally receive while under the direct care and intense physical monitoring of a medical professional.

Dynamic adaptability enables the system to work more precisely for a given patient the longer the system is being used on that patient. The system is designed to learn from the patient through analysis of the patient's historic or logged clinical measurements and is thereby able to detect patterns of change in the patient and predict the optimum adjustments needed to be made to the system. This novel feature of the system of the present invention enables the device to tailor changes in flow/oxygen that are patient specific and thereby modify or adjust the patient's oxygen exposure to safe levels. The dynamic adaptability feature of the present invention is a novel improvement over previous automatic oxygen control systems found in the prior art.

Because the dynamic adaptability feature of the present invention is logged, these logs can later be studied to look for patterns in specific disease processes, as well as over time to identify these patterns and alert care givers of changes in the patients' condition. This system presents a novel tool in studying and/or identifying respiratory diseases. The ability to study diseases with the device also would have applications in veterinary medicine in studying human diseases through animal models as well as using the device in the veterinary environment in general. The system of the present invention would also be useful in situations requiring supplemental oxygen use in industry (e.g., mining, fires, etc.), in the military (e.g., pilots, divers, etc.), and in science (e.g., space exploration, marine exploration, etc.).

BRIEF DESCRIPTION OF THE DRAWINGS

This application file contains at least one drawing executed in color. Copies of this patent application publication with color drawings will be provided by the U.S. Patent and Trademark Office upon request and payment of the necessary fee.

The accompanying drawings illustrate embodiments of the invention and are for illustration by way of example and not limitations.

DETAILED DESCRIPTION OF THE INVENTION

The present invention provides for an automatic system for use in controlling oxygen saturation ($SpO_2$) in the blood of patients placed on respiratory support. The system comprises a mechatronic device that automatically controls $SpO_2$ in the blood of a patient by automatically monitoring and adjusting the oxygen blend ($FiO_2$) and gas flow being provided to the patient. The device is mechatronic in that it comprises both mechanical and electrical components working together to provide continuous automatic adjustment of $FiO_2$ and flow of delivered gas to the patient. It should be noted that the system of the present invention also has application to other gas control systems, besides oxygen.

Figure 10:
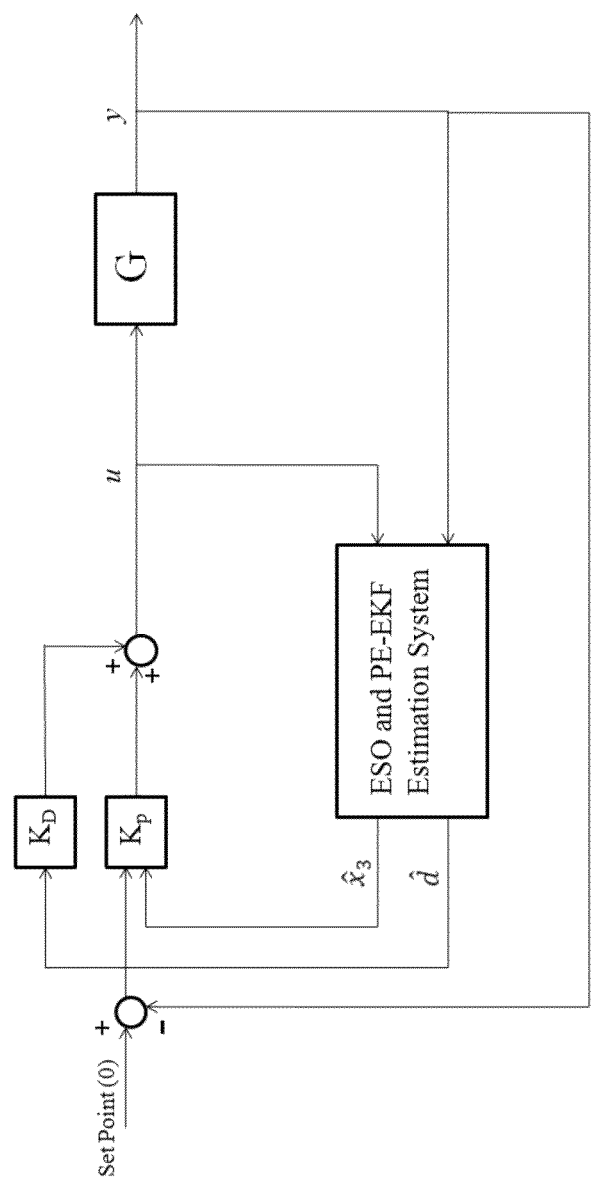
FIG. 10 is a diagram illustrating the dynamically adaptable control system with adaptive proportional gain, $K_P$, and disturbance gain, $K_D$.

The system additionally comprises a novel method for providing automatic control of $SpO_2$ in the blood of a patient with dynamic adaptability. The method comprises using an adaptive control system (as illustrated in FIG. 10) which is based on an estimation system consisting of a statistical method that includes utilization of a discrete parameter-estimating extended Kalman filter and extended state observer. The method of the present invention is adaptable to a variety of patients and provides precise control of $SpO_2$ due to the incorporation of a novel estimation system, which system estimates and determines both unknown disturbances, which cause desaturation events in the patient, and varying parameters upon receipt of signals obtained from monitoring devices connected to sensors applied to the patient. The system, through methods of the present invention, is able to adjust as required for each individual patient despite varying parameters and unknown disturbances by estimating the varying parameters and effect of the unknown disturbance(s) on the controlled parameter. Accordingly, the system and methods of the present invention enable medical professionals to provide more consistent and a higher level of care for a wide variety of patients on respiratory support.

I. Device

Figure 1:
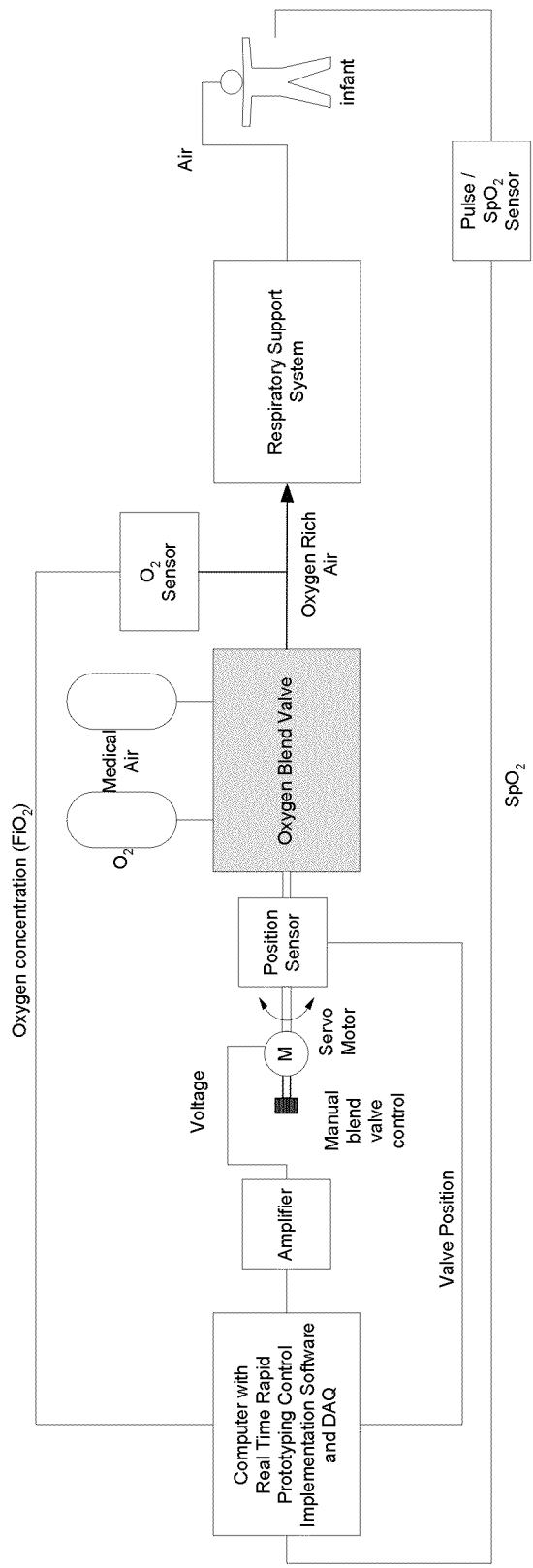
FIG. 1 is a diagram of the inventive device.
Figure 3:
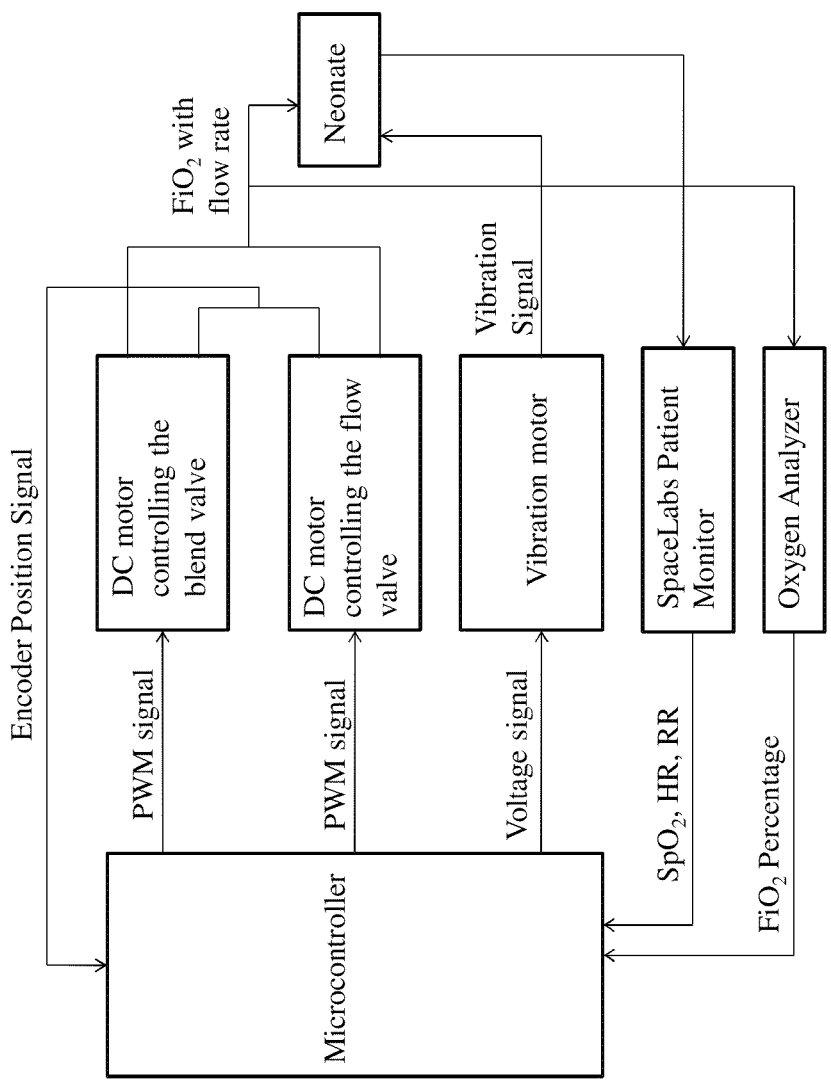
FIG. 3 is a block diagram showing the connections among the units of the control system.

The system of the present invention automatically monitors and controls $SpO_2$ in the blood of a patient through automatic adjustments to $FiO_2$ and flow of gas to the patient. The system includes a monitoring device, a microcontroller, and a device for controlling variable adjustment of $FiO_2$ using a blend valve or other means of adjusting $FiO_2$. The system may additionally or alternatively comprise a device for controlling variable adjustment of flow of gas using a flow valve or other means of adjusting flow of gas to the patient and/or a device for causing stimulation of the patient. The device of the inventive system is designed to be a servomechanism. A servomechanism, or servo, is an automatic device that uses error-sensing negative feedback to correct the performance of a mechanism. A block diagram outlining the preferred embodiment of the present invention is shown in FIG. 1. A functional diagram of the entire system is given in FIG. 3.

The monitoring device of the present invention comprises any device found in the art that is designed to measure a patient's parameters. Preferably, the monitoring device used with the present invention is selected from the group consisting of bedside monitor interface device, pulse oximeter, oxygen analyzer, and combinations thereof.

The microcontroller of the present invention is a small computer on a single integrated circuit containing a processor core, memory, and programmable input/output peripherals and which is designed for embedded applications. While microcontrollers are commonly used in automatically controlled products and devices, other devices capable of being used in lieu of a microcontroller may be used in the present invention. Preferably, the microcontroller is designed to receive signals from the monitoring device. Because $SpO_2$ levels in a patient are controlled through adjustment and regulation of $FiO_2$, and gas flow, $FiO_2$ measurement signals are sent to the microcontroller from the monitoring device. Other pertinent clinical measurements are sent to the microcontroller from the monitoring device. Both sets of measurement signals are sent to the microcontroller from the monitoring device by way of any means used in the art for inbound/outbound electronic communication, including but not limited to a serial port adapter, USB adapter, firewire, Ethernet cable and wireless communication (i.e., wi-fi). Preferably, the signals are sent to the microcontroller through a serial port adapter.

In an alternative embodiment, a monitoring device is not connected to the microcontroller and the microcontroller instead receives signals pertaining to $FiO_2$ based on the starting position of one or more valves. In such embodiments, the system is calibrated to the one or more valves prior to placing the system on a patient.

Figure 2:
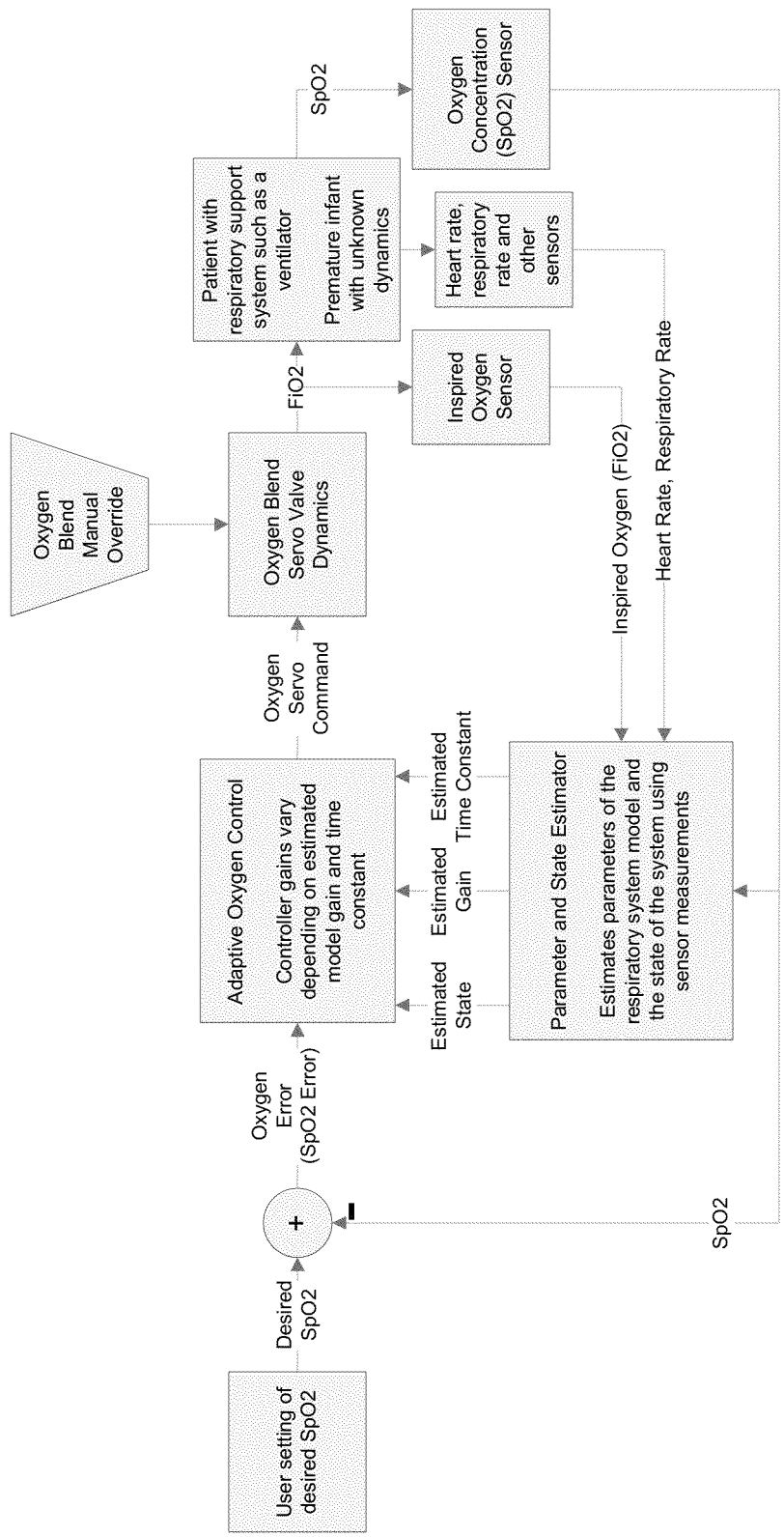
FIG. 2 is a block diagram of the adaptive oxygen control system.

In addition to the signals received from the monitoring device, the microcontroller is also designed to receive signals from a device that variably adjusts $FiO_2$ through a blend valve which blends oxygen with air to produce the desired $FiO_2$. The device controlling variable adjustment of $FiO_2$ may be any servo device used in the art to adjust a blend valve. In a preferred embodiment, the device that controls variable adjustment of $FiO_2$ comprises a servo motor. The servo motor may run on direct current (DC) or alternate current (AC). In a preferred embodiment, the servo motor is a DC motor. The servo motor controlling the adjustment of $FiO_2$ is placed in direct communication with the microcontroller by way of any means used in the art for inbound/outbound electronic communication, including but not limited to a serial port adapter, USB adapter, firewire, Ethernet cable and wireless communication (i.e., wi-fi). Preferably, the signals are sent from the microcontroller, which comprises a motor driver, to the motor via a serial port adapter. A block diagram of the oxygen control system is provided in FIG. 2.

The blend valve is manually adjusted through any means known in the art for providing manual adjustment, including but not limited to a knob, handle or dial. In the present invention, the valve is adjusted automatically by the system through use of a servo motor, which actuates the means of providing manual adjustment of the blend valve. Preferably, the manual adjustment of the blend valve is effected with a knob. A spring loaded shaft is connected to the motor shaft by a belt drive or any other mechanical drive system known in the art. The spring loaded shaft is designed to turn the blend valve knob automatically. The shaft can be easily pulled back from the knob if manual adjustment of the valve knob becomes necessary. A cylinder is attached to the end of the shaft to increase friction with the knob to allow for easier turning of the blend valve knob and less slipping. The cylinder can be fabricated from any material known in the art to increase friction. Preferably, the cylinder is comprised of rubber. The device may be connected to the shaft through the use of any attachment means known in the art. In a preferred embodiment, the device is connected to the shaft using sprockets and a timing belt. The device further comprises a built-in encoder to measure the angular position of the shaft controlling the blend valve. An encoder signal is sent from the device to the microcontroller indicating the current $FiO_2$ position of the blend valve. Based on the signals sent to the microcontroller from the patient's monitors, the microcontroller determines through algorithm whether the blend valve requires adjustment and how much adjustment is necessary.

Optionally, a second component of the device may additionally or alternatively be used to variably adjust the flow of gas delivered to the patient. The flow of gas is determined by an oxygen flow valve that may be attached to the side of the blend valve. The optional second component of the device controlling variable adjustment of gas flow may be any servo device used in the art to adjust a flow valve. In a preferred embodiment, the second component of the device variably adjusting the flow of gas to a patient through a flow valve comprises a servo motor. The servo motor may run on direct current (DC) or alternate current (AC). In a preferred embodiment, the motor is a DC motor.

The flow valve is manually adjusted through any means known in the art for providing manual adjustment, including but not limited to a knob, handle or dial. In the present invention, the flow of gas to the patient is automatically adjusted by the system through use of a servo motor, which actuates the means of providing manual adjustment of the flow valve. In a preferred embodiment, the manual adjustment mechanism (e.g., knob, handle, or dial) is replaced with a jaw coupling or other coupling means known in the art. The jaw coupling connects the flow valve to the servo motor shaft. In a preferred embodiment, manual override of the valve is provided by attachment of a means for manually adjusting the flow valve, such as a knob, handle, or dial, to enable a medical professional to manually override the flow of gas to the patient if necessary. The second servo motor further comprises a built-in encoder to measure the angular position of the flow valve.

An encoder signal from the second servo motor is then sent to the microcontroller indicating the current position of the flow valve. Based on the signals sent to the microcontroller from the patient's monitors, the microcontroller determines through learning algorithm (dynamic adaptability) whether the flow valve requires adjustment and how much adjustment of the valve is needed.

Alternatively, the devices for controlling variable adjustment of $FiO_2$ and gas flow can be used without the motors and directly interface with devices that have internal oxygen and flow controls (ventilators, SiPAP machines, etc.) thus allowing the system to interface with any respiratory support system.

The system may additionally comprise a device to stimulate the patient. Preferably, the stimulation device is attached to an extremity of the patient, preferably the foot. The device simulates tactile stimulation, which is normally provided manually by the medical professional to stimulate/remind the patient to breathe during an apneic event (using respiratory rate parameter obtained from the monitoring device). The stimulation device can be any device known in the art to provide such stimulation to a patient by placement on the patient's extremity. In a preferred embodiment, the device is a vibration motor. It is especially preferred that the vibration motor be shaftless. The stimulating device is placed in direct communication with the microcontroller by way of any means used in the art for inbound/outbound electronic communication, including but not limited to a serial port adapter, USB adapter, firewire, ribbon cable module, Ethernet cable, and wireless communication (i.e., wi-fi). Preferably, the stimulation device is in communication with the microcontroller by way of a ribbon cable module. To automatically control the stimulation device, the microcontroller additionally comprises a digital to analog converter module. The digital to analog converter module is used to send a voltage signal from the microcontroller through an analog output to a stimulation device control circuit. The circuit comprises an operational amplifier that operates as an on/off switch for the stimulation device.

The system of the present invention is designed to work with all current respiratory support modalities which include, but are not limited to: conventional mechanical ventilators, continuous positive airway pressure (CPAP), nasal CPAP (NCPAP), oral CPAP, nasal intermittent positive pressure ventilation (NIPPV) (a.k.a. NCPAP with a rate), oral IPPV, SiPAP, biphasic SiPAP, flowPAP or High Humidity Heated Flow Nasal Cannula (HHFNC), and nasal cannula.

Additionally, the ability of the system to adjust gas flow allows for a novel modality of respiratory support, HHFNC with a respiratory rate. This novel modality involves the system increasing the flow of gas for a set period of time (usually 2-3 seconds) for a set number of times (rate) in a minute. For example, a patient on 2 liters (l) of oxygen could have a set rate of 10 liters per minute (l/min) (2 second set) with flow increase of 2 l/min and the system would increase the flow to 4 l/min for 2 seconds 10 times a minute. This increase in flow could help in the treatment of apnea as well as other respiratory diseases. In treating apnea, the system can also be set to increase the flow when an apnea occurs even if the patient is not on a set rate. In addition to treating apnea, the system would also keep a log of the events which could be used in clinical treatment and/or research.

Due to the system's ability to log $FiO_2$ adjustment/monitor response data, it is useful for studying a wide array of respiratory disease processes. The system of the present invention can be used to look for patterns for predicting or differentiating disease in a variety of pulmonary disease states from bronchopulmonary dysplasia in neonates, to ARDS and pneumonia in adults. The system is also useful in the clinical setting to treat infants, children, and adults as it would minimize the patient's oxygen exposure titrating the $FiO_2$ to deliver the minimum amount of oxygen needed to keep their saturations ($SpO_2$) within the set range. As a result, patients would have less risk for oxygen toxicity, free radical generation, and tissue injury. The system of the present invention would also be useful in situations requiring supplemental oxygen use in industry (e.g., mining, fires, etc.), in the military (e.g., pilots, divers, etc.), and in science (e.g., space exploration, marine exploration, etc.). In these applications as well as many others the device would minimize the user's oxygen exposure by titrating the $FiO_2$ to deliver the minimum amount of oxygen needed to keep their saturations ($SpO_2$) within the set range. As a result, users would have less risk for oxygen toxicity, free radical generation, and tissue injury.

Laboratories would also benefit from the system as it could be used in animal labs to keep the saturations within a specific range for experimental purposes. It could also be used to study responses to medications effecting pulmonary processes, and the data from patients with specific diseases can be aggregated for computer simulations to study those diseases.

II. Dynamic Adaptability

As discussed above, the system of the present invention employs a microcontroller which enables it to process and filter clinical measurements, estimate model parameters (i.e., parameters of the dynamic system model that describe the response of the patient to inputs) and disturbances (which cause desaturation events in the patient), and use this information to control servos which adjust oxygen blend ($FiO_2$) and flow. Servos operate on the principle of negative feedback, where the control input is compared to the actual position of the mechanical system as measured by some sort of transducer at the output. Any difference between the actual and desired values (an "error signal") is amplified and used to drive the system in the direction necessary to reduce or eliminate the error.

The dynamic adaptability is a novel concept that enables the system to work more precisely for a given patient the longer the system is being used on the patient. The term "dynamic adaptability" as used herein refers to the ability of the system to adapt/make changes to its intervention decision(s) based on data reported back to the system from previous interventions in real time (dynamically). The system is designed to learn from the patient through analysis of the patient's clinical measurements and is thereby able to detect patterns of change and predict results of interventions. This novel feature of the system of the present invention is that it provides more precise changes in $FiO_2$ that are patient specific and thereby reduces the patient's oxygen exposure. The dynamic adaptability feature of the present invention is a novel improvement over previous oxygen control systems found in the prior art.

The closed loop nature of this system also ensures that the expected changes are taking place when an intervention is performed. For example, the system looks for the expected changes (based on dynamic adaptability) in the $SpO_2$ after an intervention. Preferably, the system interfaces with the monitoring device to look for the expected increase/decrease in oxygen delivery when a change is made to the amount of oxygen delivered ($FiO_2$). It also uses its error trapping algorithm(s) to distinguish from real measurements versus false measurements. This error trapping improves using dynamic adaptability the longer the system is being used on a given patient.

HHFNC (a.k.a., FlowPap) with the ability to give a rate is a new respiratory support modality that the system of the present invention provides. This feature has not been possible with any other devices. It provides caregivers with a new way to give respiratory support to their patients, and may decrease the use of other, more expensive noninvasive respiratory support devices. FlowPAP/HHFNC devices in the prior art do not have the ability to increase flow intermittently throughout a minute breathing cycle as seen in NIPPV or biphasic SiPAP. FlowPAP with a rate can be achieved by connecting a servo actuator connected to a flow control valve and can increase the flow rate above baseline for short periods of time (usually 2-3 seconds) at a user set rate per minute. The flowPAP with a rate feature can be achieved using the servo apparatus described in the paragraphs below.

The system of the present invention incorporates an adaptive microcontroller. The adaptive microcontroller is based on a learning algorithm, which is designed to improve performance of the system the longer the system is monitoring a given patient. The algorithm is based on a computer model based on real life data from patients, but it is devised to adapt to the particular patient through use of a continuously updated system model based on the patient's clinical measurements. In this sense, the system will work better for a patient the longer it is on that given patient.

To implement the system of the present invention, a monitoring device, microcontroller, and a device for controlling the variable adjustment of $FiO_2$ through a blend valve and optionally or alternatively a device for controlling the variable adjustment of gas flow through a flow vale. The devices for controlling the variable adjustment of $FiO_2$ through a blend valve and/or gas flow through a flow valve are controlled using an algorithm on the microcontroller. A computer algorithm runs on the microcontroller which includes a state estimation, disturbance estimation, and model parameter estimator filter to determine the system dynamics and update the model based microcontroller. As disclosed hereinabove, the device for controlling the variable adjustment of $FiO_2$ and/or gas flow comprises a servo motor. Alternatively, the device for controlling the variable adjustment of $FiO_2$ and/or gas flow does not comprise a motor. The algorithm determines a voltage command that is sent to an amplifier on the servo motor connected to blend valve and/or flow valve using a digital to analog converter on a DAQ card installed on the microcontroller. The amplifier provides voltage to the servo motor based on commands from the algorithm. The servo motor turns the blender valve and/or flow valve which in turn affects the $FiO_2$ and/or gas flowing to the patient. The algorithm utilizes the signals obtained from the monitoring device and position of the blend valve and/or flow valve to compute the required voltage to be sent to the respective servo motors.

Again with reference to the present invention, the signals are processed by the microcontroller through the use of software installed on the microcontroller via a computer. A feedback loop is then used to compare the measured $SpO_2$ from the patient to a desired $SpO_2$ level. If the measured $SpO_2$ differs from the desired $SpO_2$ level for the patient, an error signal is obtained on the system. The $SpO_2$ error signal serves as the input to a control algorithm, which automatically adjusts the blend valve and/or flow valve setting through use of a servo motor. Based on the signal received, an adaptive microcontroller can determine the optimal $FiO_2$ input and gas flow to maintain the prescribed level of $SpO_2$ for the patient. To change the position of either motor, a pulse width modulation (PWM) signal is sent from each motor driver in the microcontroller.

a. Discrete Parameter-Estimating Extended Kalman Filter

The system of the present invention operates with dynamic adaptability through use of a novel estimation system. The estimation system of the present invention consists of a discrete parameter-estimating extended Kalman filter and extended state observer. The extended Kalman filter is used to estimate the model parameters and the extended state observer estimates the unknown disturbances. Together these estimators provide knowledge (or at least estimates) of the parameters and disturbances. Accordingly, the system starts with varying parameters and disturbances and then use of the system on a patient enables the learning algorithm to provide estimates of the parameters and disturbances (i.e., dynamic adaptability). These estimates change as the condition of the patient changes, as well as in response to external inputs and disturbances.

The Kalman filter is a recursive state estimator which uses a linear system model in state space form to represent the dynamics of the system. The filter requires a mathematical description of the dynamic system whose states are to be estimated. The objective of the Kalman filter is to minimize estimation error. The estimation error is quantified by the error covariance matrix, P, which is updated at each iteration of the filter. The error covariance matrix contains the error covariances for each element of the state vector being estimated. The Kalman gain, K, is an optimum gain that minimizes the error covariance for each state. For a nonlinear system, the system must be linearized about an operating point before the Kalman filter can be used. When deviation for the operating point becomes too large, the performance of the Kalman filter degrades due to the reliance on a linear model. The extended Kalman filter (EKF) was linearized with respect to the state estimates at the current iteration thus allowing for convergence over a larger range within the state space for nonlinear systems.

The filter was able to converge over one hour sections of data with the 5 second time step, but the R value had to be increased to 120. The error covariance of the time constant did not approach zero due to the Kalman gain being limited by high R value. To improve the performance of the filter and convergence of the error covariance, the continuous PE-EKF was converted to a discrete version of the filter for the present invention. The filter assumed a nonlinear discrete system defined as:

$$x_k = f_{k-1}(x_{k-1}, u_{k-1}, w_{k-1})$$

$$y_k = h_k(x_k, v_k)$$

$$w_k \sim (0, Q_k)$$

$$v_1 k \sim (0, R_1 k)$$

The equations for the discrete PE-EKF were taken from D. Simon, *Optimal State Estimation*, Hoboken, N.J.: John Wiley and Sons, Inc., 2006 and were given as:

$$P_k^- = F_{k-1} P_{k-1}^+ F_{k-1}^T + L_{k-1} Q_{k-1} L_{k-1}^T$$

$$\hat{x}_k^- = f_{k-1}(\hat{x}_{k-1}^+, u_{k-1}, 0)$$

$$K_k = P_k^- H_k^T (H_k P_k^- H_k^T + M_k R_k M_k^T)^{-1}$$

$$\hat{x}_k^+ = \hat{x}_k^- + K_k[y_k - h_k(\hat{x}_k^-, 0)]$$

$$P_k^+ = (I - K_k H_k) P_k^-$$

where the $F_{k-1}$, $L_{k-1}$, $H_k$, and $M_k$ matrices were found using the nonlinear system $$P = \begin{bmatrix} 1 & 0 & 0 \\ 0 & 40 & 0 \\ 0 & 0 & 10 \end{bmatrix}$$

$$\hat{x} = \begin{bmatrix} 0 \\ 50 \\ 3.5 \end{bmatrix}$$

and were defined as:

$$F_{k-1} = \left.\frac{\delta f_{k-1}}{\delta x}\right|_{\hat{x}_k^+}$$

$$L_{k-1} = \left.\frac{\delta f_{k-1}}{\delta w}\right|_{\hat{x}_k^+}$$

$$H_k = \left.\frac{\delta h_k}{\delta x}\right|_{\hat{x}_k^-}$$

$$M_k = \left.\frac{\delta h_k}{\delta v}\right|_{\hat{x}_k^-}$$

These equations were applied to a first-order system model assumption. One modification was made to the system model used in the continuous PE-EKF when implementing the discrete PE-EKF. The time constant parameter augmented state, x2, was inverted to ensure that if the state converged to a value of zero that the output values would not become infinite. The new state was derived as $$\hat{x}_2 = \frac{1}{x_2}$$

$$\dot{\hat{x}}_2 = -\frac{1}{x_2^2}\dot{x}_2 = \hat{x}_2^2 w_p$$

Using the equations for the discrete PE-EKF taken from Simon, the continuous nonlinear system model $$\left[\dot{SpO}_2 = -\frac{1}{\tau}SpO_2 + \frac{G_p}{\tau}FiO_2\right]$$

was modified to become the following equations:

$$\dot{\tilde{x}}_1 = -\tilde{x}_2 x_1 + \tilde{x}_2 x_2 u + w$$

$$\dot{\tilde{x}}_2 = -\tilde{x}_2^2 w_p$$

$$\dot{\tilde{x}}_3 = w_p$$

$$y = x_1 + v$$

The continuous nonlinear equations are then converted to discrete equations which were given as:

$$x_1(1,k+1) = x_1(1,k) + \Delta t(-x\hat{}_1(2,k)x_1(1,k) + x\hat{}_1(2,k)x_1(3,k)u_1k + w_1k)$$

$$\tilde{x}_{2,k+1} = \tilde{x}_{2,k} + \Delta t(\tilde{x}_{2,k}^2 w_{p,k})$$

$$x_{3,k+1} = x_{3,k} + \Delta t w_{p,k}$$

$$y_k = x_{1,k} + v_k$$

Using the discrete nonlinear system model equations above, the F, L, H, and M matrices were given as $$F_{k-1} = \left.\begin{bmatrix} 1 - \hat{x}_2\Delta t & \Delta t(-\hat{x}_2 + x_3 u) & \Delta t\hat{x}_2 u \\ 0 & 1 - 2\hat{x}_2 w_p \Delta t & 0 \\ 0 & 0 & 1 \end{bmatrix}\right|_{\hat{x}_k^+}$$

$$L_{k-1} = \left.\begin{bmatrix} q\Delta t & 0 & 0 \\ 0 & 1 + \hat{x}_2^2 \Delta t & 0 \\ 0 & 0 & \Delta t \end{bmatrix}\right|_{\hat{x}_k^+}$$

$h_k = [1\, 0\, 0]$ $M_k = 1$

Figure 4:
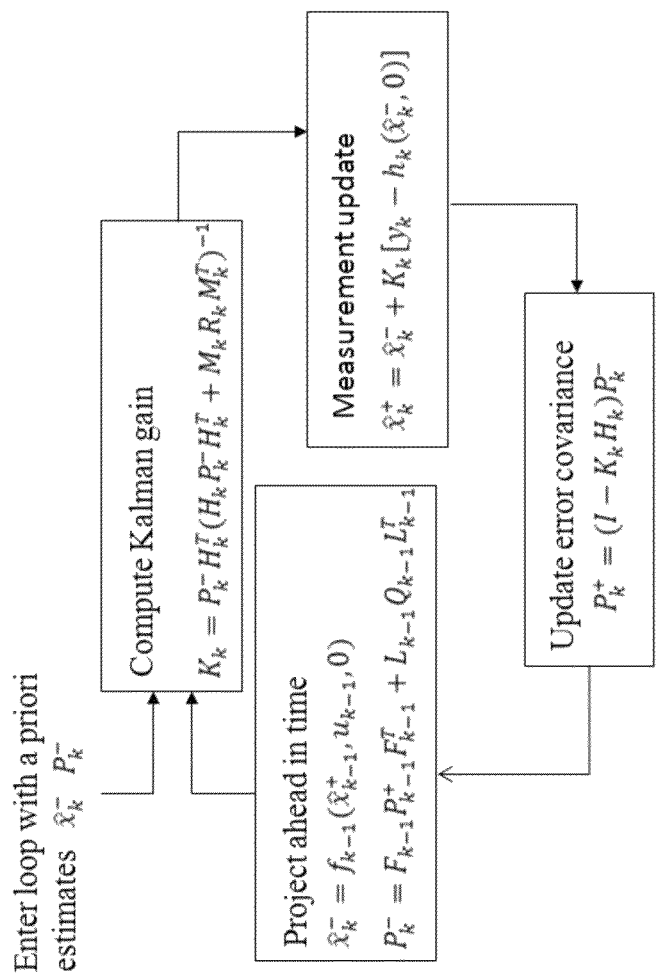
FIG. 4 is a diagram of how the discrete PE-EKF updates for each iteration.

The F and L matrices were updated at each time step with the a priori state estimates while the H and M remained constant. A diagram of how the discrete PE-EKF updates operate can be seen in FIG. 4.

Figure 5:
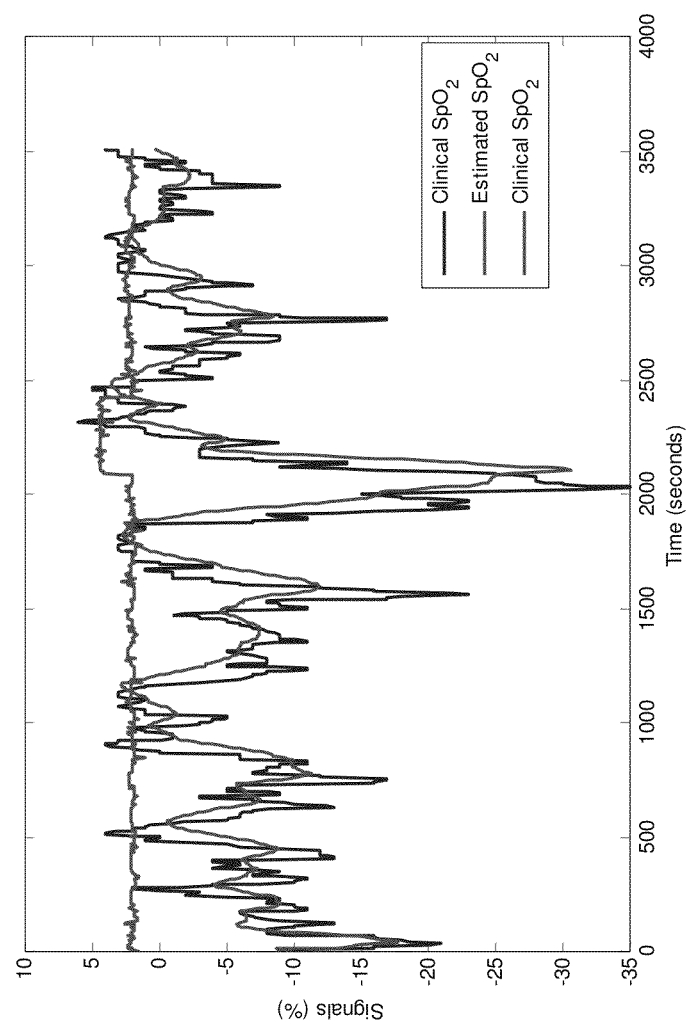
FIG. 5 illustrates SpO$_2$ and FiO$_2$ signals obtained from patient data with the x1 state from the discrete PE-EKF for a one hour section of data.
Figure 6:
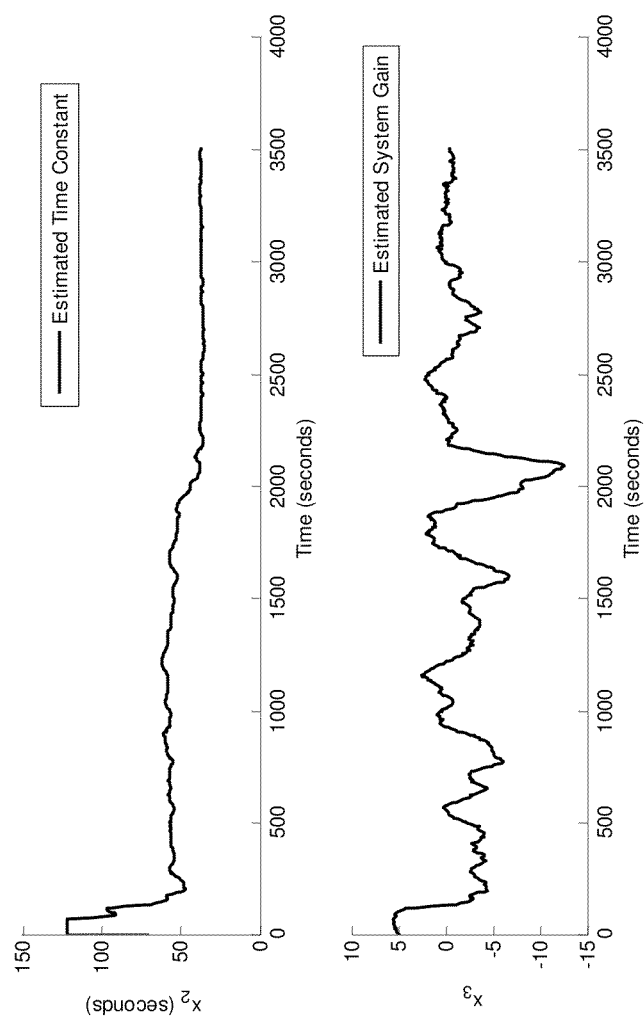
FIG. 6 is a graphical illustration of the estimated time constant, $x_2$, and estimated system gain, $x_3$, from the discrete PE-EKF for a one hour section of patient data.
Figure 7:
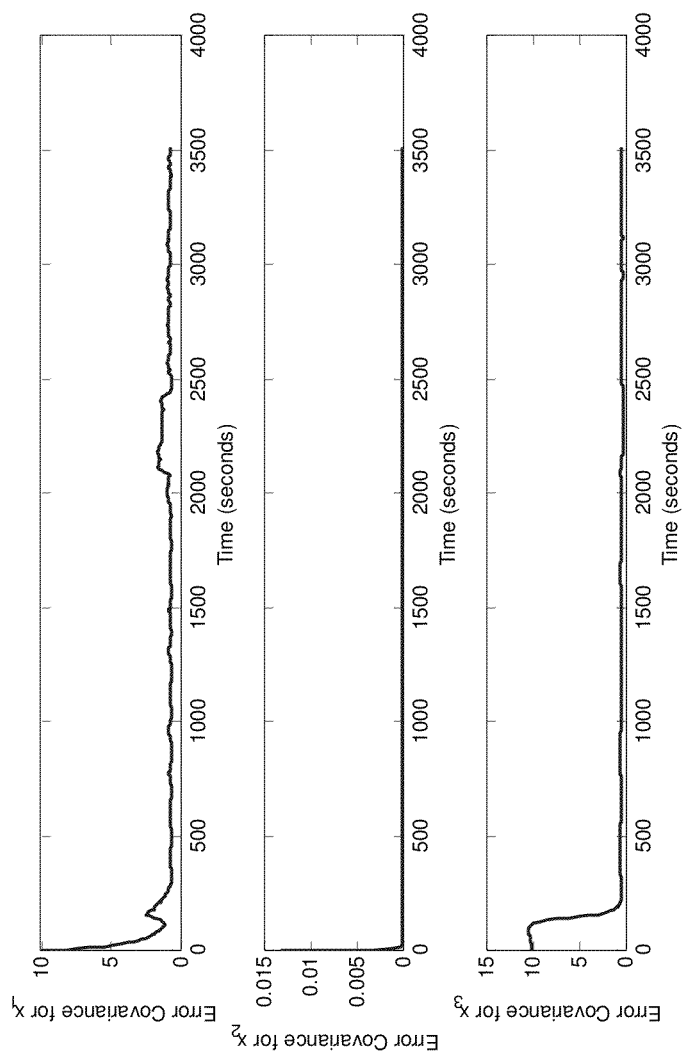
FIG. 7 is a graphical illustration of the error covariance for each state from the discrete PE-EKF filter for a one hour section of patient data.

The discrete filter is then executed on one hour sections of patient data with a time step of 5 seconds. The covariance of the measurement noise, Rk, for the filter is 10% $SpO_2$ and the covariance of the process noise, Qk, is 0.001% $SpO_2$. The nominal signal values were subtracted from the $FiO_2$ and $SpO_2$ signals (the nominal values, 22% and 90% respectively are subtracted.) This subtraction was done so that the signals were perturbations from nominal conditions. The initial conditions were implemented for the filter as:

$$P_0^+ = \begin{bmatrix} 10 & 0 & 0 \\ 0 & 10 & 0 \\ 0 & 0 & 10 \end{bmatrix}$$

$$\hat{x} = \begin{bmatrix} SpO_{2_o} - 90 \\ 4.3073 \\ \frac{1}{76.9693} \end{bmatrix}$$

where $SpO_2$, is the initial value of the $SpO_2$ data set. The initial error covariance values were chosen as smaller values since some knowledge of the parameters was known. The initial estimated $SpO_2$ value was chosen as the initial deviation from the nominal $SpO_2$ value. The estimated system parameters were initialized as the mean values of the ranges found by the continuous PE-EKF. The estimated time constant had saturation limits imposed so the estimate would stay between 31.8138 and 122.1249 seconds. If these limitations were not included, the estimated time constant would approach unrealistic values. The estimated $SpO_2$ compared with the clinical $SpO_2$ can be seen in FIG. 5. The estimated parameters can be seen in FIG. 6. The error covariance for each state can be seen in FIG. 7. The discrete PE-EKF converged on each hour of patient data with a five second time step with the reduced R value unlike the continuous implementation. The error covariance for the time constant approached zero for the discrete filter whereas the error did not in the continuous case. The discrete PE-EKF displayed the same issue that the system gain was estimated as a negative because the control signal stayed constant when the $SpO_2$ level dropped due to unknown disturbances.

b. Discrete Extended State Observer

Due to unknown disturbances causing negative estimated system gains with the PE-EKF, a discrete extended state observer (ESO) was applied to the input $FiO_2$ and output $SpO_2$ to estimate the unknown disturbances. Some disturbance estimators were designed to handle slight perturbations for a modeled system. The discrete ESO was designed to remove the requirement of a modeled system by rejecting un-modeled dynamics so that the dynamics appear in the disturbance estimation portion. Desaturation events are often being caused by unknown disturbances to the infant. Using the ESO to estimate disturbances could give greater insight into what happens to the infant during desaturation periods.

The equations for the discrete ESO were taken from Miklosovic et al., "Discrete Implementation and Generalization of the Extended State Observer," presented at the Proceedings of the 2006 American Control Conference, Minneapolis, Minn., 2006, and Radke, "On Disturbance Estimation and Its Application in Health Monitoring," Cleveland State University, 2006. The discrete time system was expressed as:

$$\hat{x}_{k-1} = \phi \hat{x}_k + \Gamma u_k$$

$$\hat{y}_k = H\hat{x}_k + Ju_k$$

where $\phi$, $\Gamma$, $H$, and $J$ are found using the A, B, C, and D state space matrices from the continuous state space system model and using the c2d.m program in Matlab to form the discrete system. The discrete ESO was given as:

$$x\hat{}_1(k-1) = \phi x\hat{}_1 k + \Gamma u_1 k + L_1 p(y_1 k - y\hat{}_1 k)$$

$$\hat{y}_k = H\hat{x}_k + Ju_k$$

where $y_k$ is the measured $SpO_2$ signal. To improve performance, the following substitution was made to the state vector:

$$x_1 k = x\hat{}_1 k + L_1 c(y_1 k - y\hat{}_1 k)$$

where $$L_c = \phi^{-1} L_p$$

Substituting the discrete ESO equation into the substituted state vector gives $$\hat{x}_{k-1} = \phi \bar{x}_k + \Gamma u_k$$

$$\hat{y}_k = H\hat{x}_k + Ju_k$$

The gain, $L_c$, was designed so the eigenvalues of the estimator were always at the same location. The eigenvalues of the discrete ESO were given by $$\lambda(z) = |z1 - (\phi - \phi L_c H)|$$

The eigenvalues were chosen by $$\lambda(z) = (z - \beta)^2$$

where $$\beta = e^{-w_o T}$$

where T is the time step and $w_o$ is a single bandwidth tuning parameter. The gains that place the eigenvalues at the desired location were given as:

$$L_c = \begin{bmatrix} 1 - \beta^2 \\ \dfrac{(1 - [(\beta)])^2}{T} \end{bmatrix}$$

Figure 8:
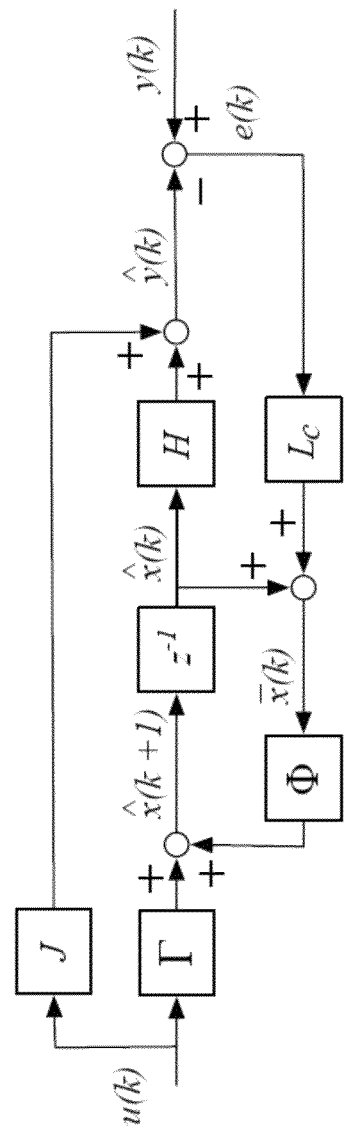
FIG. 8 is a block diagram of the discrete ESO.

The input-output form of the estimator was:

$$\hat{x}_{k+1} = [\phi - L_p H]\hat{x}_k + [\Gamma - L_p J \cdot L_p] u_{d_k}$$

$$y_{d_k} [1 - L_c H]\hat{x}_k + [-L_c J \cdot L_c] u_{d_k}$$

where $u_{d_k}$ is the combined input of the control signal and measurement and $y_d$ is the output. A block diagram of the estimator system can be seen in FIG. 8.

c. Discrete Extended State Observer and Kalman Filter Estimation System

Figure 9:
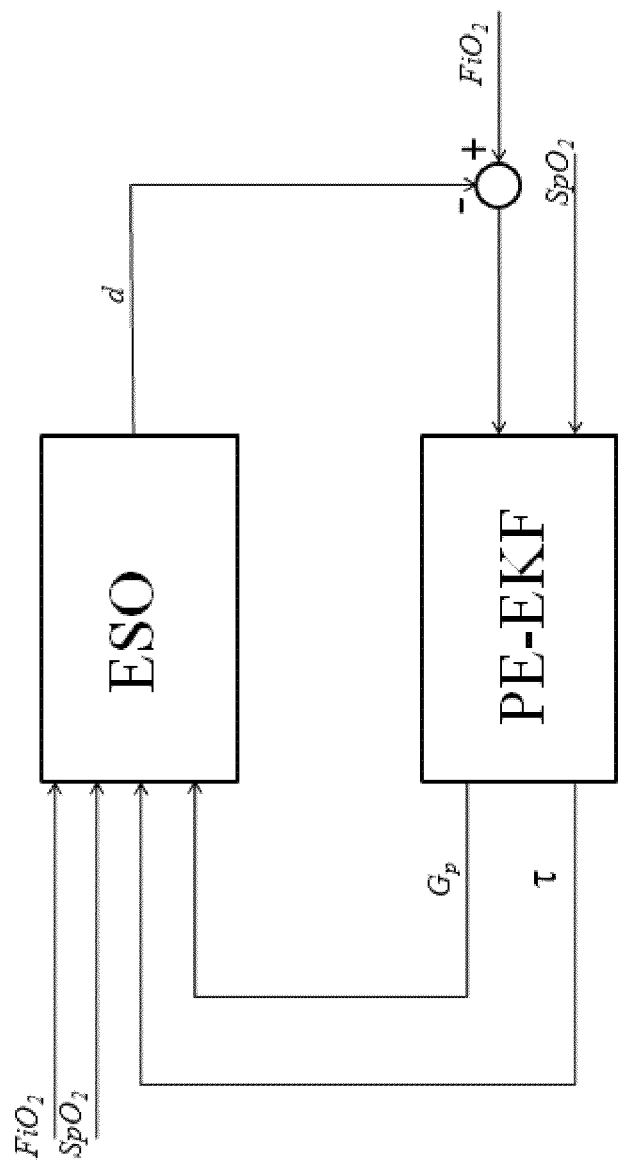
FIG. 9 is a diagram showing how the ESO and PE-EKF update with each iteration.

The discrete ESO needed accurate parameters to be able to accurately estimate the disturbances in the system. The discrete PE-EKF estimated negative system gain values because it had no knowledge of the disturbances that were affecting the system. By modifying the control signal with the estimated disturbance, the parameter estimations from the Kalman filter were more accurate and stayed in the positive range. By updating the parameters inside the ESO, the estimated disturbance gave a closer estimation to the actual disturbance in the system. A diagram for the new estimation system of the discrete ESO and PE-EKF can be seen in FIG. 9.

The A, B, C, D matrices for the discrete ESO were modified to include the estimates from the PE-EKF. The new matrices were defined as:

$$A = \begin{bmatrix} -\bar{X}_2 & \bar{X}_2 \hat{X}_3 \\ 0 & 0 \end{bmatrix}$$

$$B = \begin{bmatrix} \bar{X}_2 \hat{X}_3 \\ 0 \end{bmatrix}$$

$$C = [1 \ 0]$$

$$D = 0$$

where $\tilde{x}_2$ is the estimated inverse of the time constant, $\tau$, and $\hat{x}_2$ is the estimated system gain, $G_P$, from the PE-EKF. With this change of variables in the formulation of the system for the discrete ESO, the filter still had an observability matrix with a rank of two showing that the system is observable. The discrete ESO gain, $L_c$, is updated with each iteration with the updated parameters from the PE-EKF.

The control signal to the PE-EKF was modified by the estimated disturbance output from the ESO. The new control input for the PE-EKF was determined to be $$u_{EKF} = u + \hat{d}$$

where $\hat{d}$ is the estimated disturbance from the ESO, $u$ is the control signal, and $u_{EKF}$ is the modified control signal used for analysis in the discrete PE-EKF. The control signal was only modified by the disturbance estimate if the estimate was a negative value. If the disturbance estimate was positive, the control signal to the PE-EKF was the measured $FiO_2$. The discrete PE-EKF still fulfilled the detectability condition since all of the states had stable eigenvalues.

An adaptive control system developed based on the discrete ESO and PE-EKF estimator system is further described in the present invention. A block diagram of the control system can be seen in FIG. 10. In the FIG. 10, G, represents the dynamic respiratory system being controlled. The output $SpO_2$, y, is fed back to the set point and an error signal is created by subtracting the $SpO_2$ from the set point thus creating a closed loop system. The set point for the control system is 0% since the $SpO_2$ data is subtracted by a nominal value of 90% which is a safe level for the premature infant. This error signal is fed into the first proportional control block. The maximum allowable steady state error for a proportional control system is given as $$e_{ss} = \frac{1}{1 + G_{DC} K_P}$$

where $e_{ss}$ is the maximum allowable steady state error and $G_{DC}$ is the system gain. By rearranging the above equation and substituting in the estimated steady state system gain, the control gain for the error signal, $K_p$, is given as $$K_p = \frac{\frac{1}{e_{ss}} - 1}{\hat{x}_3}$$

where $\hat{x}_3$ is the estimated steady state system gain from the discrete PE-EKF. The maximum steady state error is chosen to be 5%. At each iteration, the control gain, $K_p$, is updated with the estimated system gain from the discrete PE-EKF. A second control gain, $K_D$, is multiplied by the estimated disturbance from the discrete ESO. The control gain, $K_D$, in the preferred system is set to a constant value of 0.4. This control gain is found by trial and error balancing the need for stability and disturbance rejection. The control signal based on the error signal is added to the disturbance based control signal to form the total control effort:

$$u(t) = d(t)K_D + (y(t) - y_{ref})K_p$$

The automated system of the present invention possessing dynamic adaptability simulates the level of care that patients, especially premature infants, traditionally receive while under the direct care and intensive monitoring of a medical professional. It is important to note that the automatic control design of the inventive system is not a replacement for and does not inhibit human monitoring or interaction. The system of the present invention preserves the present caution and warning alarm system currently used by devices in the art and also provides a manual override that would allow a medical professional to adjust the blend valve by hand and disengage the automatic system. There are also audible and visual alarms built into the inventive system to alert medical professionals when manual intervention is necessary. The system also double checks the set alarms for the monitoring device and alerts the medical professionals when the alarms are not set at proper levels. For example, if the system is set to maintain $SpO_2$ between 85-92%, the patient's $SpO_2$ is 95%, and an alarm has not been emitted, the system of the present invention would signal an alarm to alert the medical professionals that the monitoring device alarm parameters must be checked. Calibration steps are also required to be taken by the medical professional when placing the system on a patient to ensure that the system correctly adjusts the valves.

The system of the present invention is adaptable to any form of respiratory support and does not require a ventilator in order to function. However, the system can interface with ventilators and other equipment either directly or manually. Use of the automatic control system of the present invention decreases equipment cost as well as resource cost and enables the system to be much more flexible so as to potentially have a role in the home health environment as well as hospital. The system is also adaptable to non-medical uses, including but not limited to use in industry, military, aviation, etc.

The system of the present invention also has the capability to increase the flow rate during an apneic spell to try to stimulate the patient and recover them from the apnea. This is a novel improvement over systems in the prior art and has wide applications in the treatment of sleep apnea, apnea of prematurity, and other forms of apnea.

The dynamic adaptability feature of the present invention is also logged and these logs can later be studied to look for patterns in specific disease processes, as well as over time to identify these patterns and alert care givers of changes in the patients' condition. This system presents a novel tool in studying and/or identifying respiratory diseases. The ability to study diseases with the device also would have applications in veterinary medicine in studying human diseases through animal models as well as using the device in the veterinary environment in general. The system of the present invention would also be useful in situations requiring supplemental oxygen use in industry (e.g., mining, fires), in the military (e.g., pilots, divers), and in science (e.g., space exploration).

DEFINITIONS

To facilitate understanding of the invention, several terms are defined below.

The term "patient" as used herein is defined as including but not being limited to: a person or animal requiring medical care, a person or animal receiving medical care or treatment, a person or animal under a physician's care for a particular disease or condition, a person or animal who is awaiting for or undergoing medical treatment or care, and combinations thereof.

The term "signals" as used herein refers to a patient's clinical measurements.

The term "clinical measurements" as used herein refers to measurements regarding $FiO_2$, $SpO_2$, as well as vital signs.

The term "vital signs" as used herein includes but is not limited to heart (or pulse) rate, blood pressure, and respiration rate.

The term "parameters" as used herein refers to the dynamic characteristics of the patient's response to inputs.

The term "patient response" or "response of the patient" as used interchangeably herein refers to the time varying output signals of the patient.

The term "varying parameters" as used herein refers to differences in parameters as among patients. For example, an infant patient will have parameters that are different from those of an adult patient.

The term "unknown disturbances" as used herein is in reference to processes or signals that adversely affect that which is being controlled but are not able to be predicted both in regard to when they may occur and how severe they may affect the controlled parameter. For example, in the control of $SpO_2$ certain events could occur, such as sudden decrease of heart rate, which would have an adverse affect on the patient's $SpO_2$.

When introducing elements of the present invention or the preferred embodiments(s) thereof, the articles "a," "an," "the" and "said" are intended to mean that there are one or more of the elements. The terms "comprising," "including" and "having" are intended to be inclusive and mean that there may be additional elements other than the listed elements.

As various changes could be made in the above system and methods without departing from the scope of the invention, it is intended that all matter contained in the above description and in the examples given below, shall be interpreted as illustrative and not in a limiting sense.

EXAMPLES

1. Testing of Discrete ESO for Disturbance Estimation Performance

The discrete ESO was tested for disturbance estimation performance by using data from a model simulation. The continuous A, B, C, and D matrices of the continuous state space system were given as $$\begin{bmatrix} \dot{x}_1 \\ \dot{\hat{d}} \end{bmatrix} = A \begin{bmatrix} x_1 \\ \hat{d} \end{bmatrix} + Bu$$

$$y = C \begin{bmatrix} x_1 \\ \hat{d} \end{bmatrix} + Du$$

$$A = \begin{bmatrix} -\frac{1}{\tau} & \frac{G_p}{\tau} \\ 0 & 0 \end{bmatrix}$$

$$B = \begin{bmatrix} \frac{G_p}{\tau} \\ 0 \end{bmatrix}$$

$$C = [1\ 0]$$

$$D = 0$$

The state vector consisted of the estimated $SpO_2$, $x_1$, and the estimated disturbance, $\hat{d}$. Using the A and C matrices, the observability matrix was formed. The rank of the observability matrix was two which corresponded to the number of estimated states, so the discrete ESO was observable.

Figure 11:
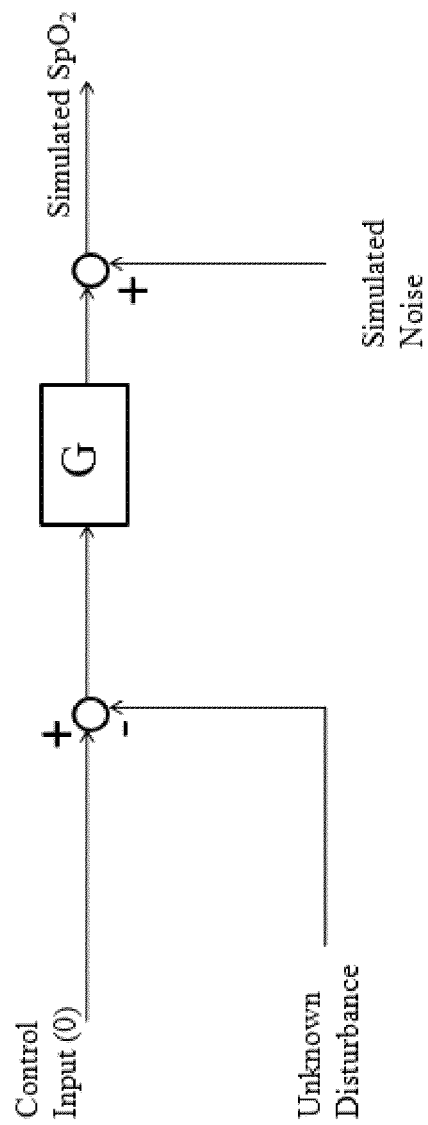
FIG. 11 is a diagram of the system used to create SpO$_2$ data from the model simulation that is used to test the discrete ESO.
Figure 12:
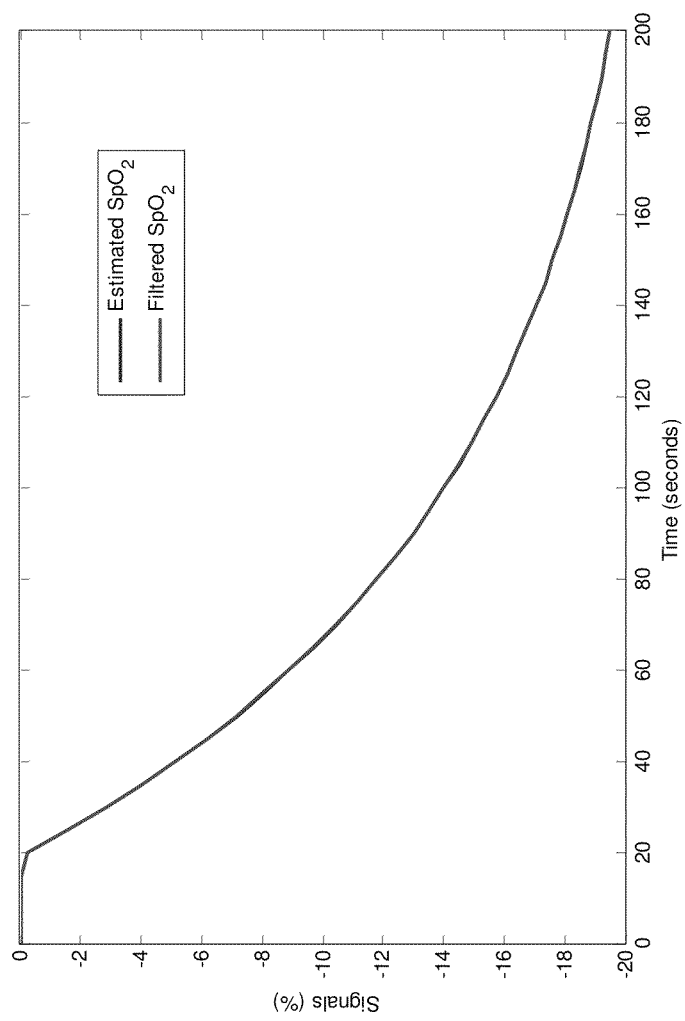
FIG. 12 is a graph illustrating the estimated and actual SpO$_2$ using the discrete ESO with a 5 second time step with data from the model simulation.
Figure 13:
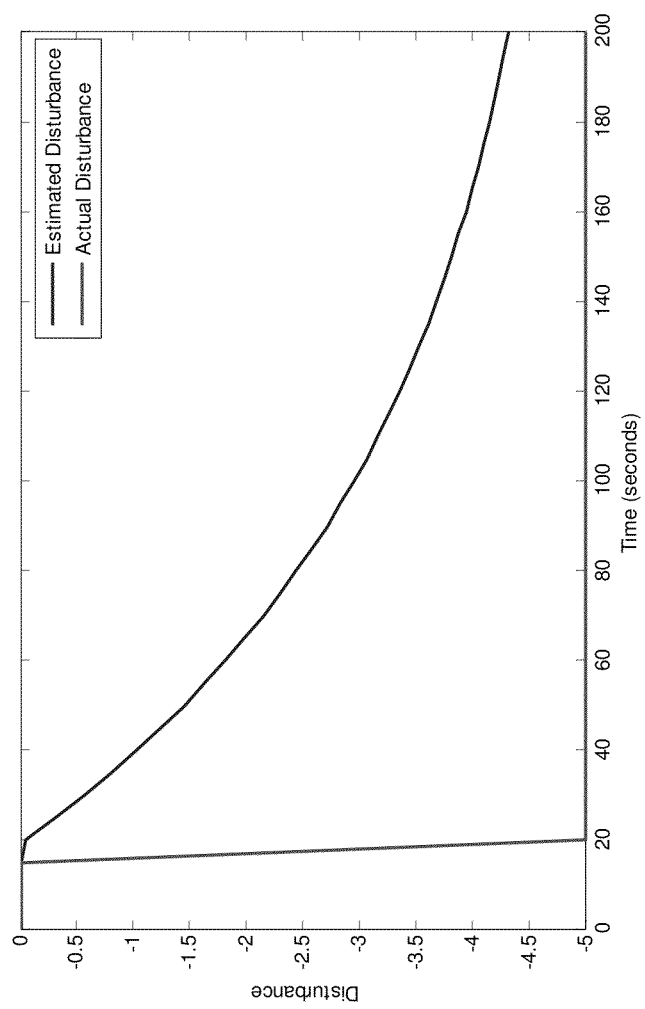
FIG. 13 illustrates the actual and estimated disturbances using the discrete ESO for a 5 second time step with data from the model simulation.
Figure 14:
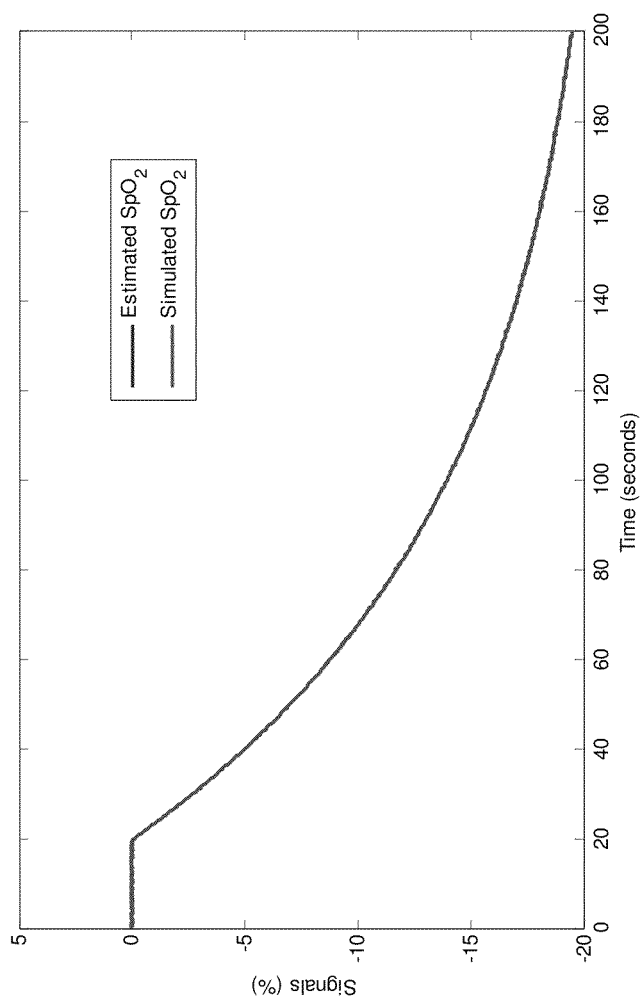
FIG. 14 illustrates the actual and estimated $SpO_2$ using discrete ESO with a 0.1 second time step with data from the model simulation.
Figure 15:
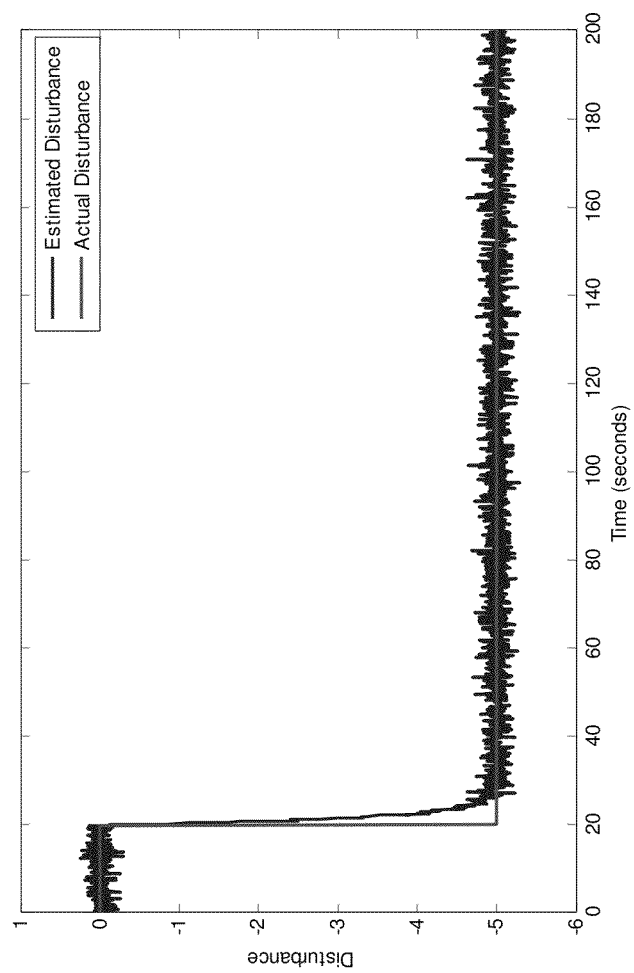
FIG. 15 illustrates the actual and estimated disturbances using the discrete ESO for a 0.1 second time step with data from the model simulation.

The performance of the discrete ESO for disturbance estimation was first tested with input-output data that was created using Simulink. A Simulink diagram that was used to create the input-output data can be seen in FIG. 11. The first test using data from the model simulation was with a first-order system with a constant system gain and a time constant. The tuning parameter, $w_o$, was chosen to be 300 which resulted in the best performance of the observer. The system gain and time constant for the simulation and estimator were 4.3073 and 76.9693 seconds. The input control signal was zero for the entire test. An unknown disturbance was added to the control signal. The unknown disturbance was a 5% step down at 20 seconds into the simulation. The time step for this test was 5 seconds which would have been seen by the measurement equipment used in the clinical setting. The estimated $SpO_2$ converged onto the actual $SpO_2$ which can be seen in FIG. 12. The estimated disturbance was unable to match the actual disturbance from the simulation due to the large time step and can be seen in FIG. 13. The time step was reduced on the simulation data until the estimated disturbance captured the actual disturbance in the system. A time step of 0.1 was chosen to be as large as possible while accurately estimating the disturbances. The estimated $SpO_2$ converged onto the actual $SpO_2$ and can be seen in FIG. 14. The estimated disturbance accurately matched the actual disturbance with the 0.1 second time step and can be seen in FIG. 15.

2. Second Test of Discrete ESO for Disturbance Estimation Performance

Figure 16:
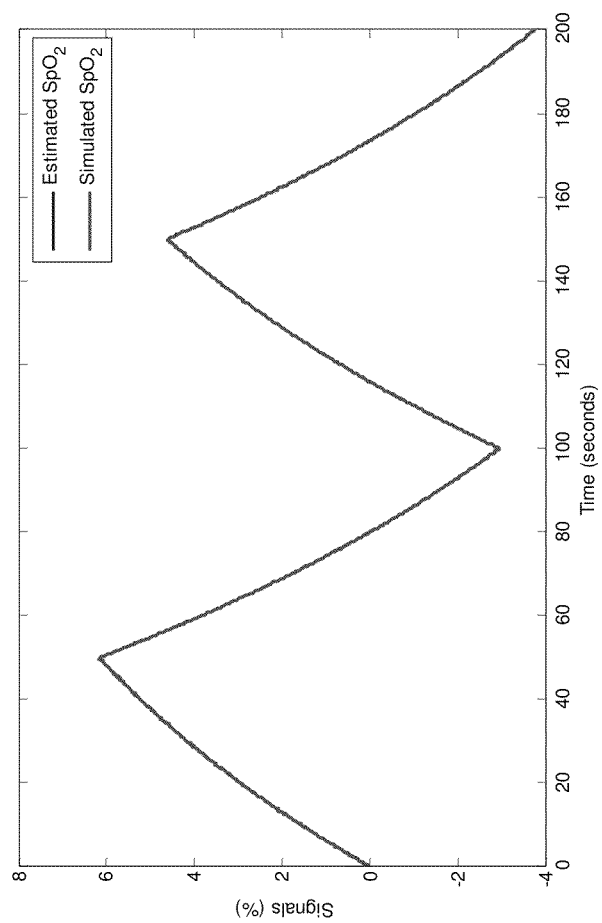
FIG. 16 illustrates the actual and estimated $SpO_2$ using discrete ESO with a 0.1 second time step with data from the model simulation.
Figure 17:
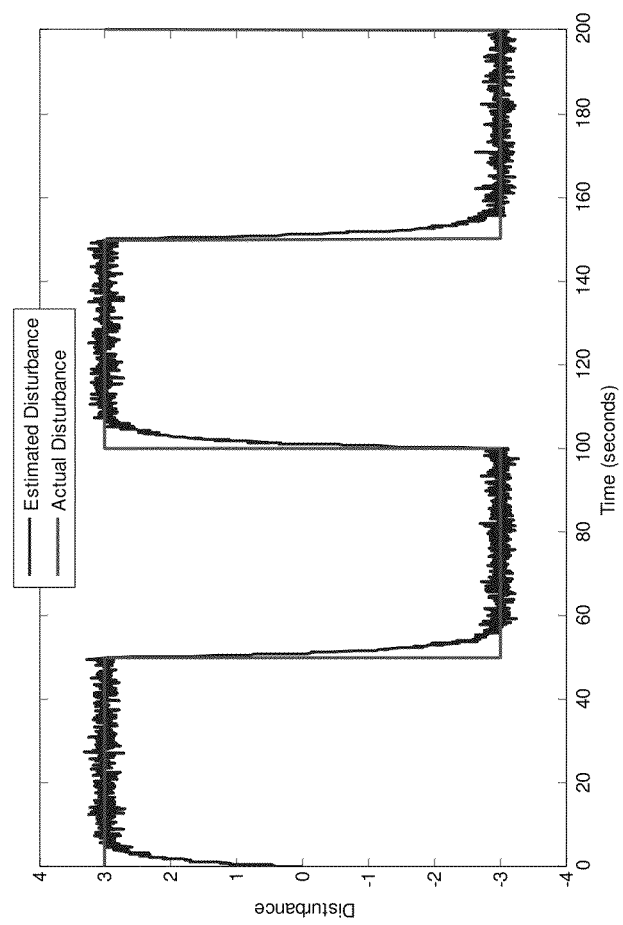
FIG. 17 illustrates the actual and estimated disturbances using the discrete ESO with a 0.1 second time step with data from the model simulation.

The second test with data from the simulated model was also conducted with a constant system gain and time constant. The system gain and time constant for the simulation and estimator were 4.3073 and 76.9693 seconds. The input control signal was again zero for the entire test. An unknown disturbance was added to the control signal. The unknown disturbance was a square wave oscillating at 0.01 Hz with an amplitude of 3. The time step for this test was 0.1 seconds. The estimated $SpO_2$ again converged onto the actual $SpO_2$ and this graph can be seen in FIG. 16. The estimated disturbance correctly estimated the actual disturbance taken from the simulation and can be seen FIG. 17.

Figure 18:
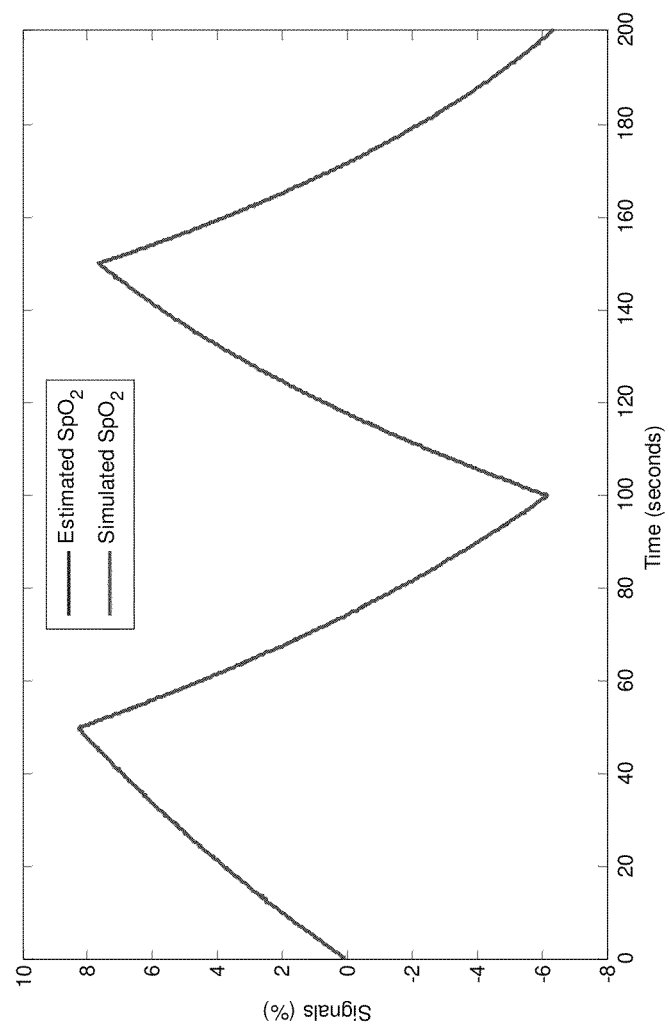
FIG. 18 illustrates the actual and estimated $SpO_2$ with the system parameters that are different from the data simulation and ESO.
Figure 19:
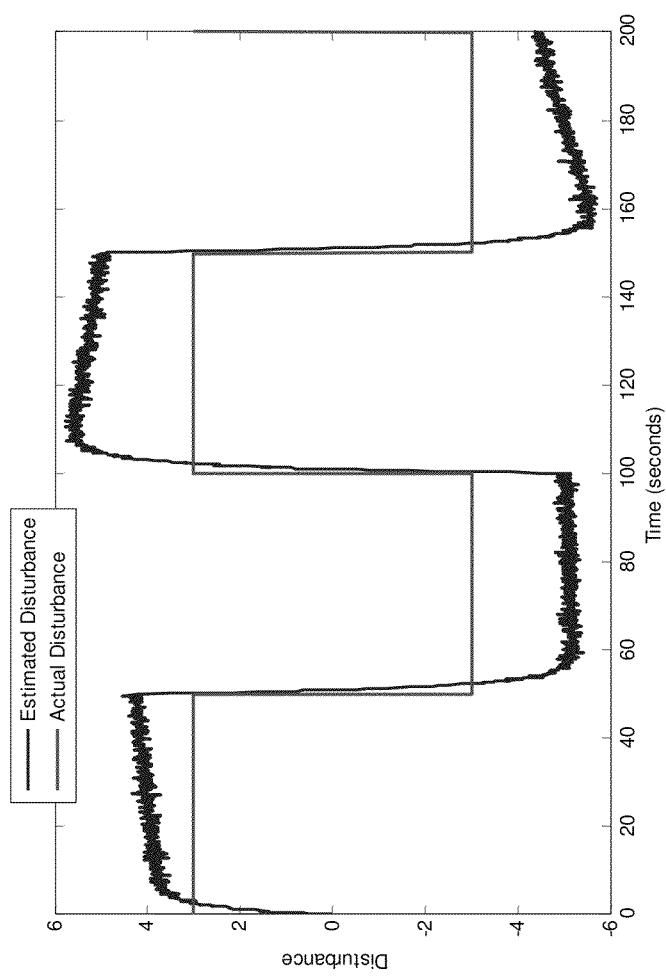
FIG. 19 illustrates the actual and estimated disturbances with system parameters that are different from the data simulation and ESO.

Each of these tests (in Example 1 and Example 2) showed the ability of the discrete ESO to estimate the $SpO_2$ and the disturbance that the system was experiencing. An issue with the discrete ESO was that the parameters of the system must be known in order to produce accurate disturbance estimates. The system gain and time constant in the discrete ESO equations were kept constant at 4.3073 and 76.9693 seconds in the previous simulations. The simulation for the system model had a system gain and time constant that were both sine waves that were used vary the parameters in the next simulation. The square wave disturbance was used again in this test. The estimated $SpO_2$ converged onto the $SpO_2$ from the model simulation and can be seen in FIG. 18. The estimated disturbance does not match the actual disturbance since the parameters for the discrete ESO do not match the parameters used in the simulation. The actual and estimated disturbances can be seen in FIG. 19.

3. Testing of Discrete ESO for Convergence on Actual Patient Data

Figure 20:
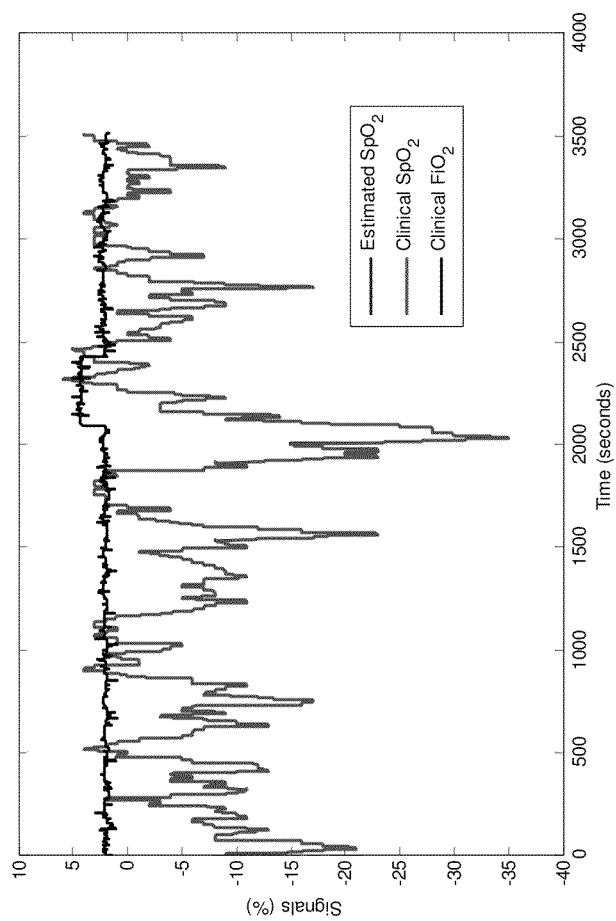
FIG. 20 illustrates the estimated and actual $SpO_2$ from the discrete ESO and patient data with the control signal $FiO_2$.
Figure 21:
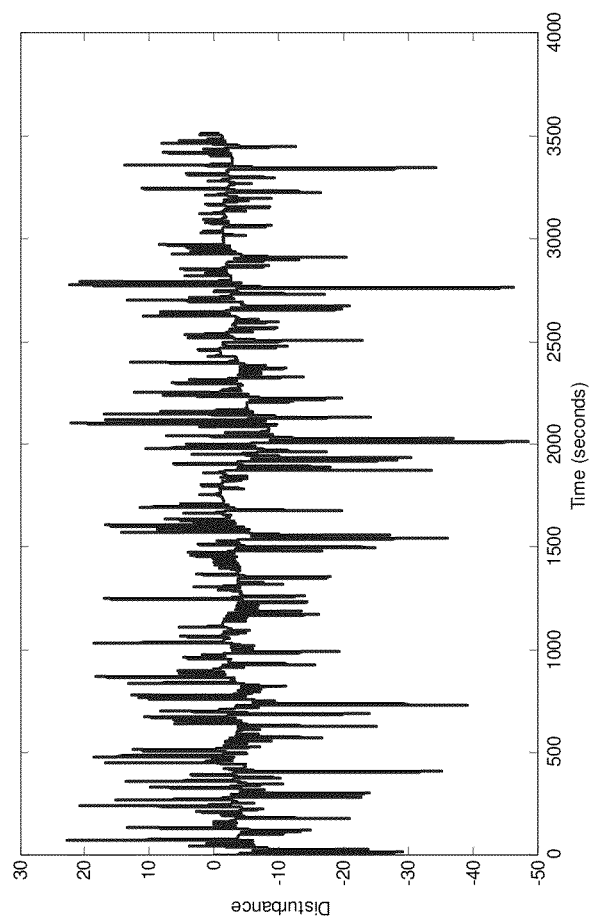
FIG. 21 illustrates the estimated disturbance from the discrete ESO that was run on a one hour section of patient data.
Figure 22:
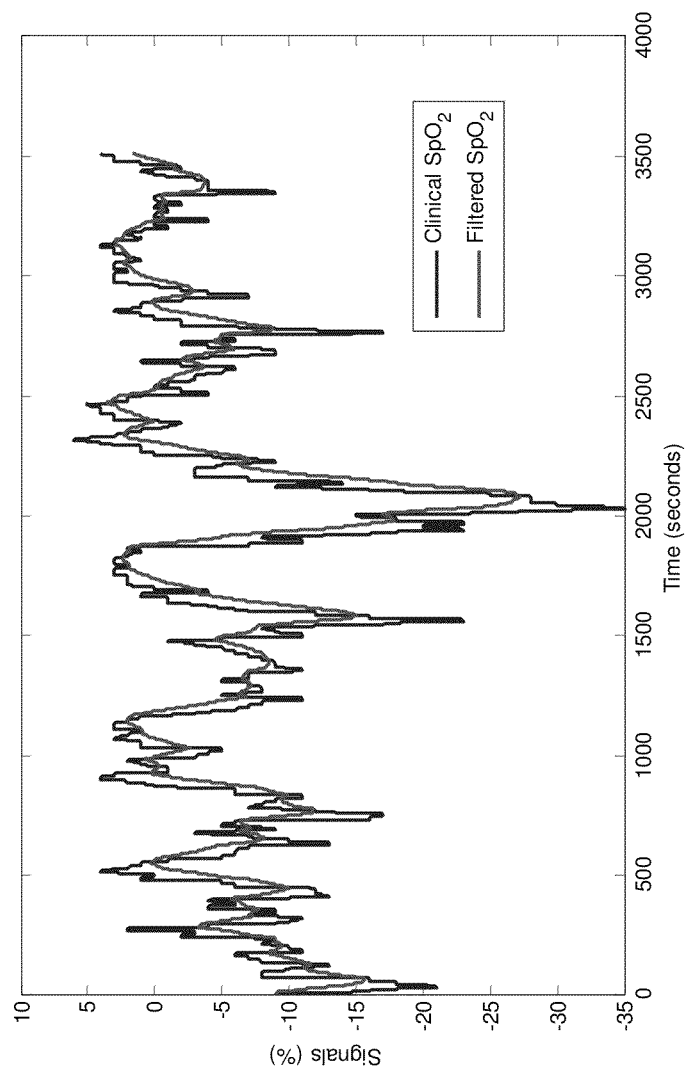
FIG. 22 illustrates the actual $SpO_2$ and the filtered $SpO_2$ after the use of a low pass filter.
Figure 23:
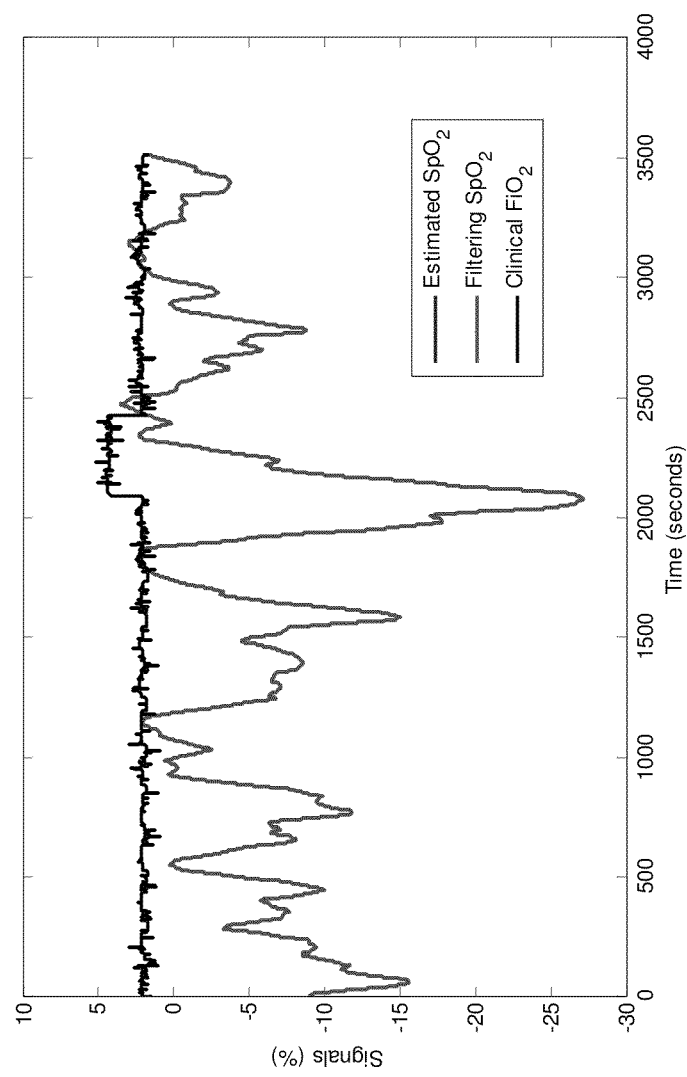
FIG. 23 illustrates the filtered $SpO_2$ from patient data and estimated $SpO_2$ from the discrete ESO with a time step of 0.1 seconds.
Figure 24:
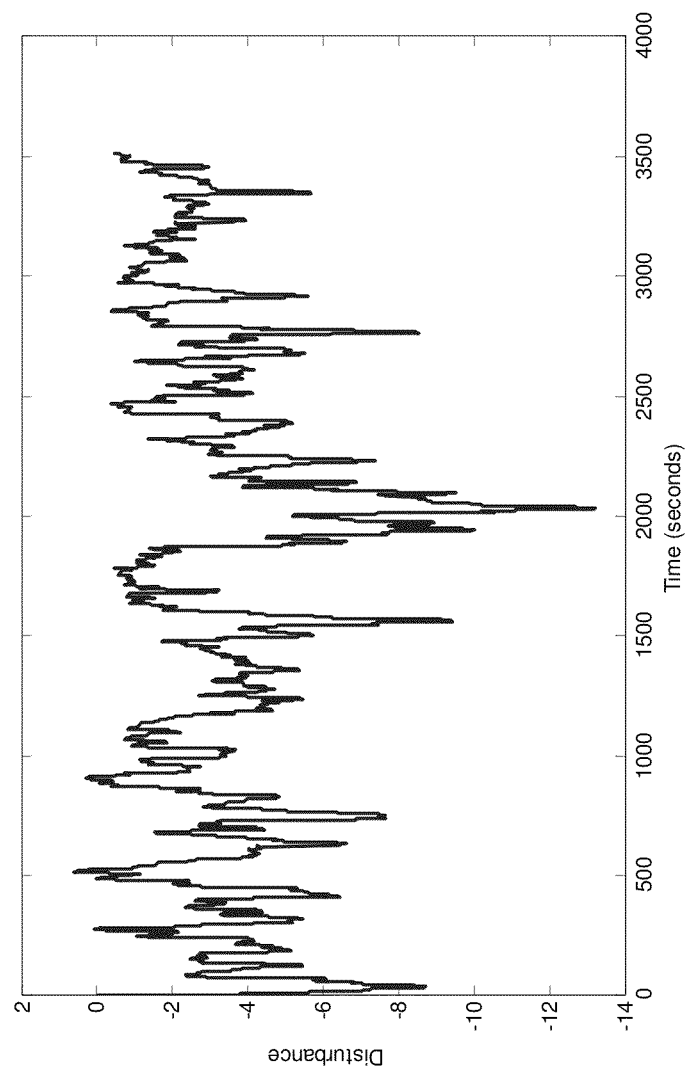
FIG. 24 illustrates the estimated disturbance from filtered patient data from the discrete ESO with a 0.1 second time step.

The performance of the discrete ESO was then tested for convergence on actual patient data. A one hour section of patient data was used to evaluate the performance of the discrete ESO to estimate disturbances. The system gain and time constant were chosen to be 4.3073 and 76.9693 seconds which were the mean values of the range of system parameters. The time step was chosen to be 0.1 seconds due to the convergence of the estimated disturbance in simulation testing. The tuning parameter, wo, for the discrete ESO was chosen to be 300. The estimated $SpO_2$ once again converged on the actual $SpO_2$ and this graph can be seen in FIG. 20. The estimated disturbance can be seen in FIG. 21. The estimated disturbance produced large peaks that were caused by noise present in the system. The ESO system matched the $SpO_2$ data and the unmodeled dynamics and disturbances were lumped into the estimated disturbance, but the noise was also included. The $SpO_2$ patient data was measured with a Masimo pulse oximeter with an error range of ±3%. A discrete low pass filter was applied to the $SpO_2$ signal of the patient data before the discrete ESO is used. The discrete low pass filter was given as $$SpO_{2_{f,k+1}} = SpO_{2_{f,k}} + \Delta t \left( -\frac{SpO_{2_{f,k}}}{40} + \frac{SpO_{2_k}}{40} \right)$$

where $SpO_{2_f}$ was the filtered $SpO_2$ data and $SpO_2$ was the actual $SpO_2$ taken from the patient data. The time step for the discrete low pass filter was also 0.1 seconds. The value 40 was chosen after testing multiple values to adequately filter the patient $SpO_2$. The filtered $SpO_2$ was compared to the actual $SpO_2$ values taken from patient data (see FIG. 22). The discrete ESO was then tested on the same one hour section of patient data with the discrete low pass filter to see how the low pass filter improves the performance of the estimated disturbance. The estimated $SpO_2$ converged on the filtered $SpO_2$ data which can be seen in FIG. 23. The estimated disturbance did not produce large peaks and exhibited behavior more in tune with the desaturation events present in the patient data and can be seen in FIG. 24.

4. Testing of Estimator System

Figure 25:
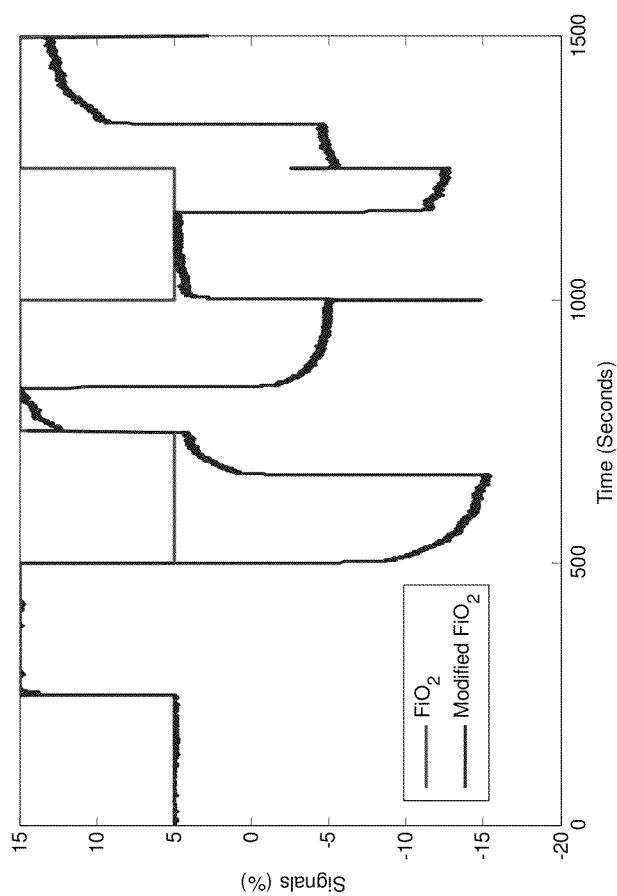
FIG. 25 illustrates the $FiO_2$ from simulated data used in the discrete ESO and the modified $FiO_2$ signal sent to the discrete PE-EKF.
Figure 26:
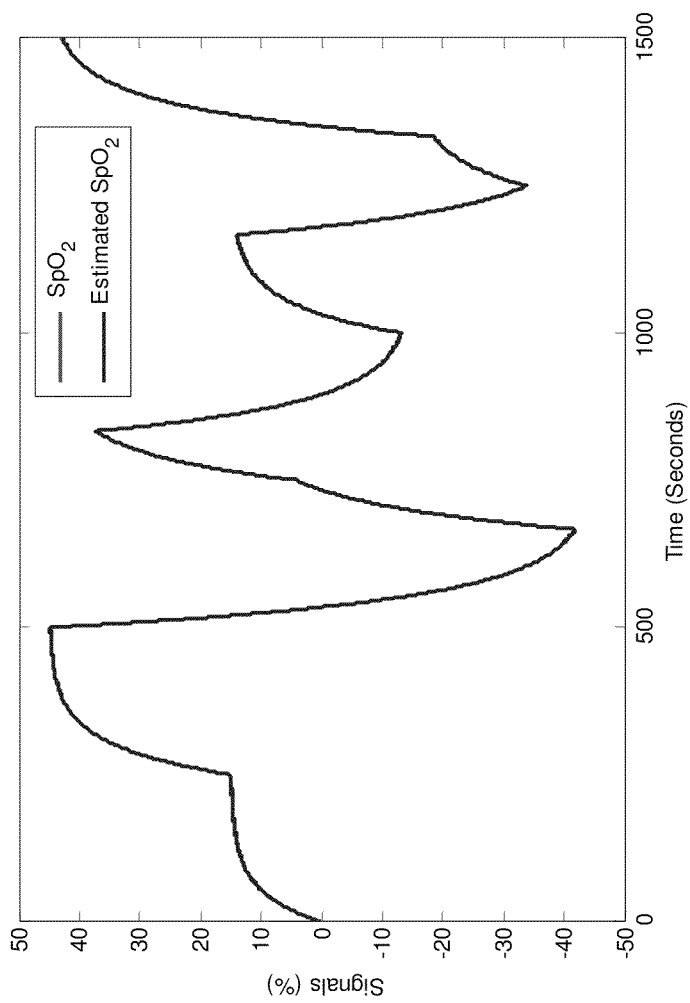
FIG. 26 illustrates the $SpO_2$ from the model simulation with the estimated $SpO_2$ from the discrete ESO.
Figure 27:
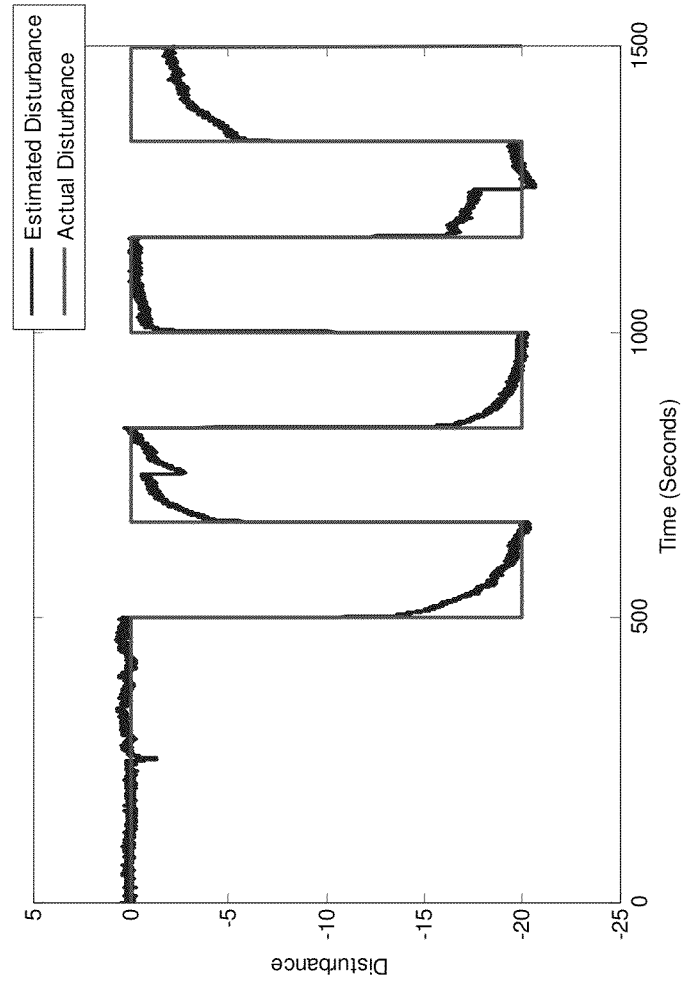
FIG. 27 illustrates the estimated disturbance from the discrete ESO with the actual disturbance in the simulated system.
Figure 28:
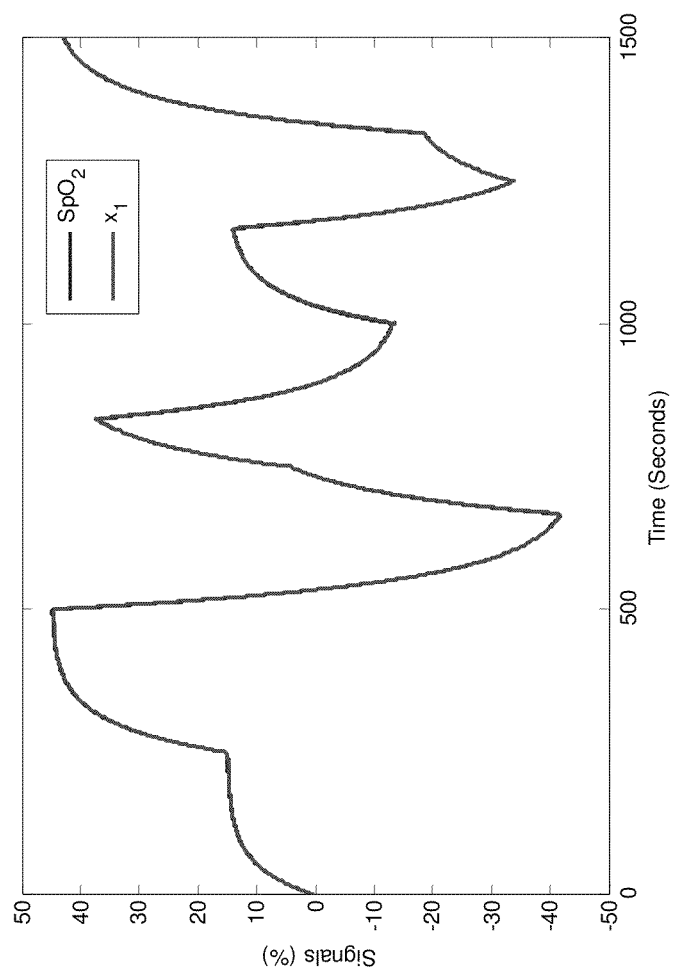
FIG. 28 illustrates the estimated $SpO_2$ from the discrete PE-EKF with the $SpO_2$ from the model simulation.
Figure 29:
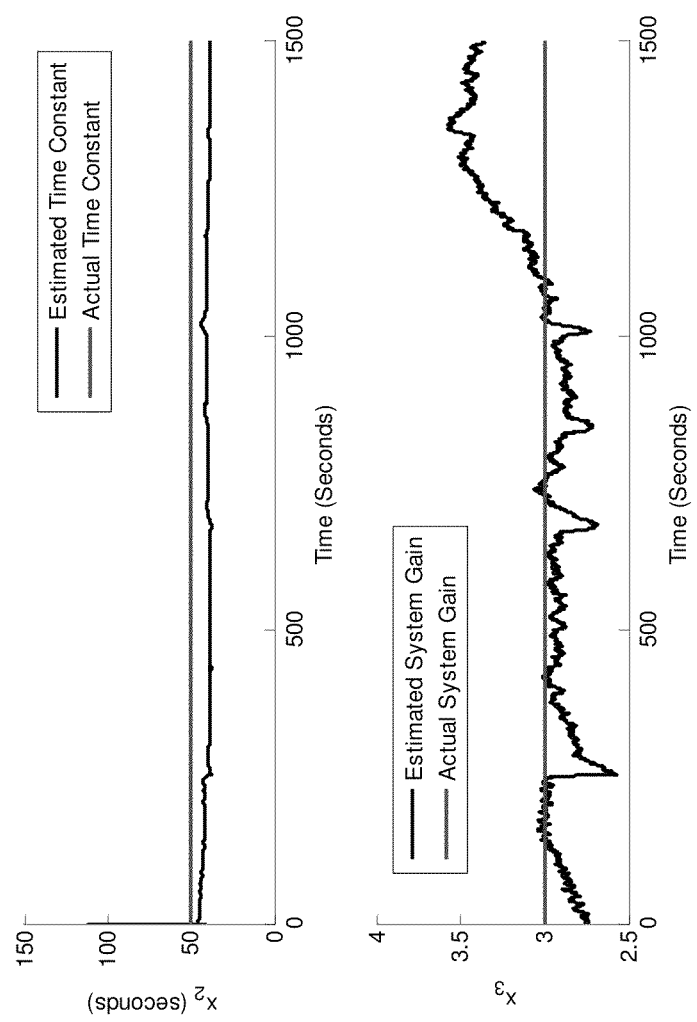
FIG. 29 illustrates the estimated time constant and system gain from the discrete PE-EKF for the simulated data.
Figure 30:
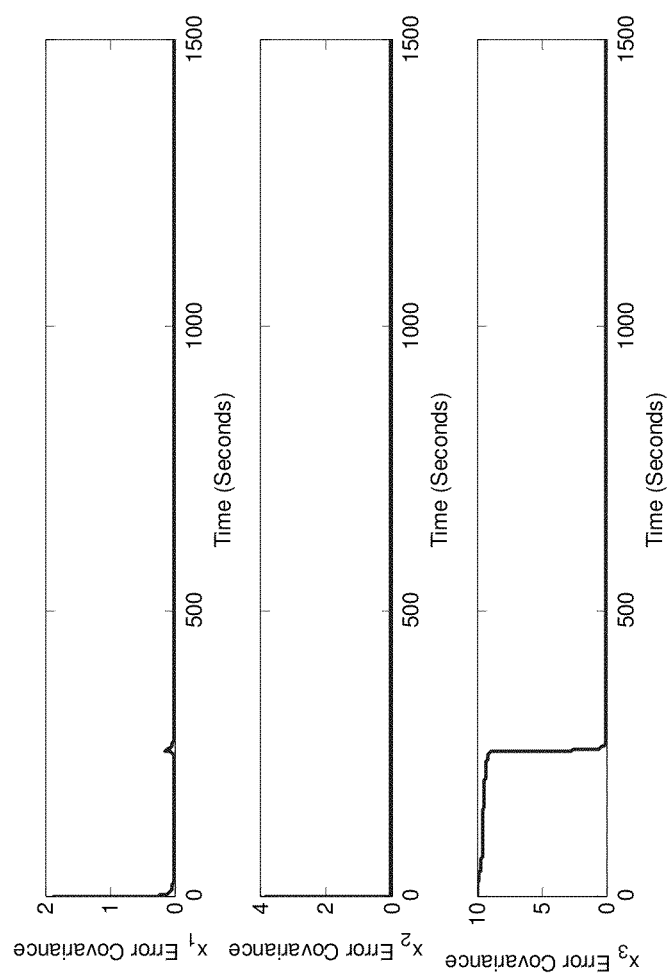
FIG. 30 illustrates the error covariance for each state from the discrete PE-EKF.
Figure 31:
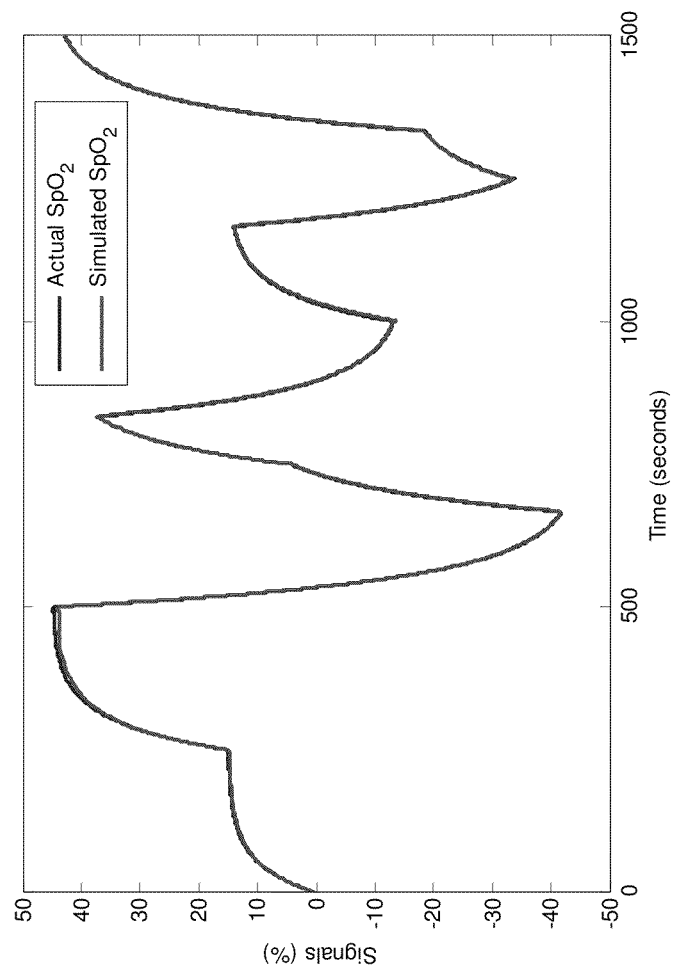
FIG. 31 illustrates the $SpO_2$ from the model simulation using the estimates for the disturbance and system parameters matching the actual $SpO_2$.

The estimator system was first tested on data from a simulated model. First, the estimator system was run with a non varying time constant and system gain. The time constant had a value of 50 seconds and the system gain had a value of 3. The FiO$_2$ input to the system was a square wave with an oscillating frequency of 0.002 Hz and an amplitude of 10. The disturbance started at 200 seconds and was also a square wave with a frequency 0.003 Hz and an amplitude of 10. The simulation was run for 1500 seconds. The tuning parameter, w$_o$, for the ESO was set to 300. The initial conditions for the PE-EKF were $$\hat{x} = \begin{bmatrix} SpO_{2_o} \\ 0.022 \\ 3.3 \end{bmatrix}$$

$$P = \begin{bmatrix} 10 & 0 & 0 \\ 0 & 10 & 0 \\ 0 & 0 & 10 \end{bmatrix}$$

where SpO$_{2_o}$ was the first point of the SpO$_2$ data set. The PE-EKF had a covariance for the process noise, Q$_k$, of 0.001% SpO$_2$ and a covariance of the measurement noise, R$_k$, of 2% SpO$_2$. The 0.1 second time step was used for the simulation and the estimator system. The FiO$_2$ from the simulated model and the modified control, u$_{EKF}$, that was used by the PE-EKF can be seen in FIG. 25. The estimated SpO$_2$ from the ESO converged onto the SpO$_2$ data from the model simulation and can be seen in FIG. 26. The estimated disturbance was compared with the actual disturbance to the system can be seen in FIG. 27. The estimated SpO$_2$ from the discrete PE-EKF can be seen in FIG. 28. The estimated time constant and gain was compared with the actual parameters can be seen in FIG. 29. The error covariance for each state of the discrete PE-EKF converged to small values and can be seen in FIG. 30. After the estimates for the disturbance and system parameters were found, the system model was simulated again and was compared to the SpO$_2$. The equation for the system model was $$\dot{\hat{z}} = -\hat{x}_2 z + \hat{x}_1 \hat{x}_2 (u + \hat{d})$$

where z was the SpO$_2$ from the simulation. The SpO$_2$ from the model simulation matched the actual SpO$_2$ and this plot can be seen in FIG. 31. The estimates of the disturbance and system parameters were not the exact values, but the combination of the three estimates provided an accurate relationship between the input and output of the model.

5. Testing of Estimator System with Varying Time Constants

Figure 32:
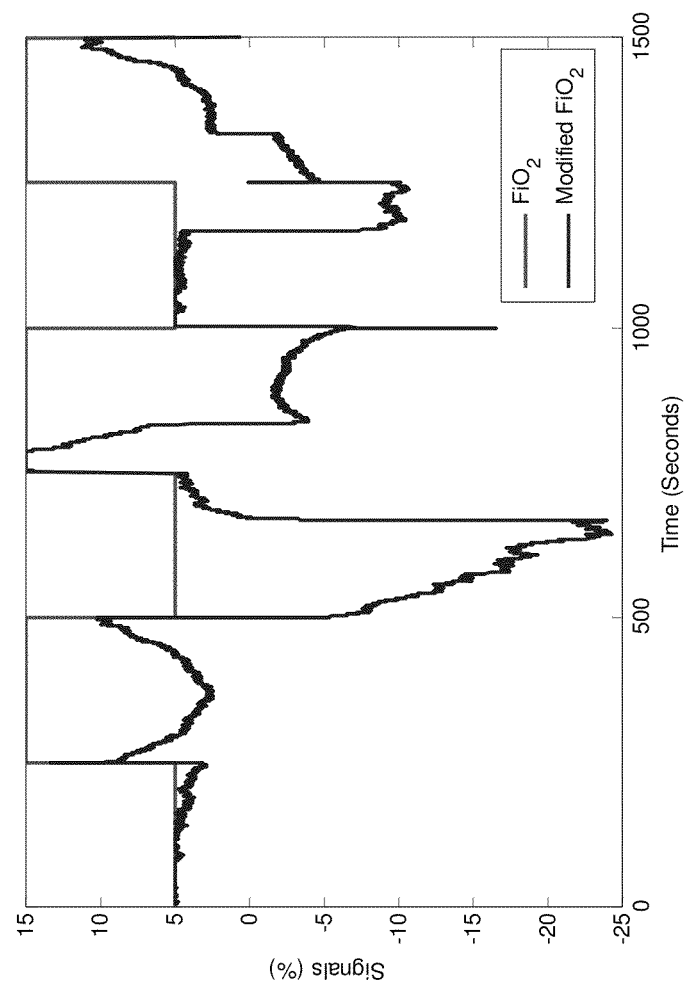
FIG. 32 illustrates the actual $FiO_2$ used by the discrete ESO and modified $FiO_2$ used by the discrete PE-EKF for the varying parameters test.
Figure 33:
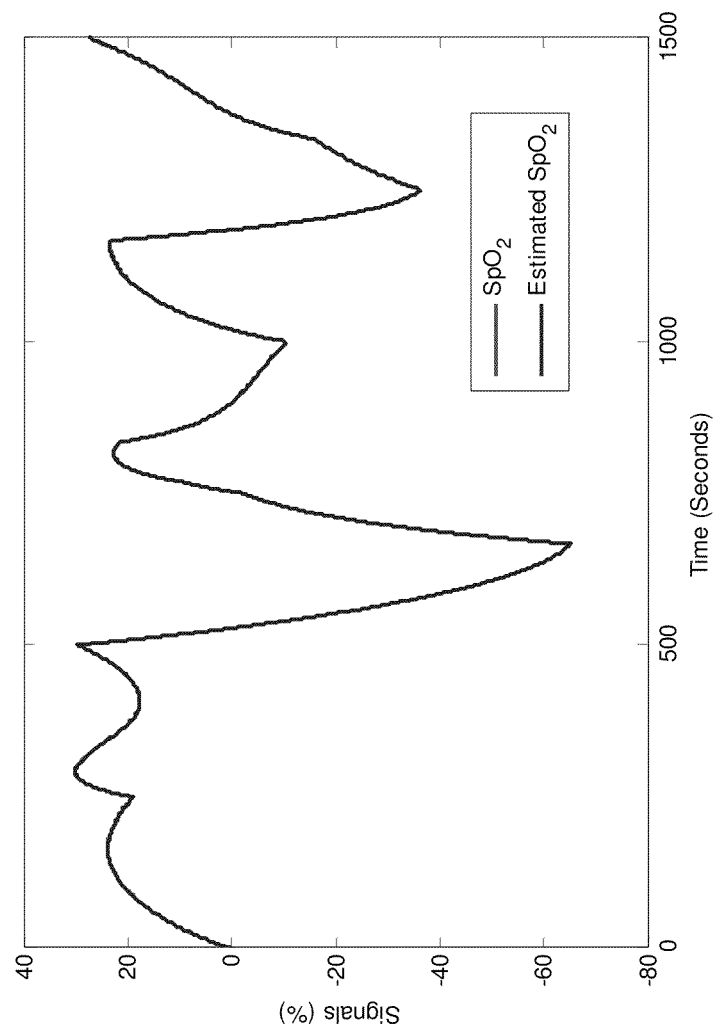
FIG. 33 illustrates the estimated $SpO_2$ from the discrete ESO compared to the actual $SpO_2$ for the varying parameters test.
Figure 34:
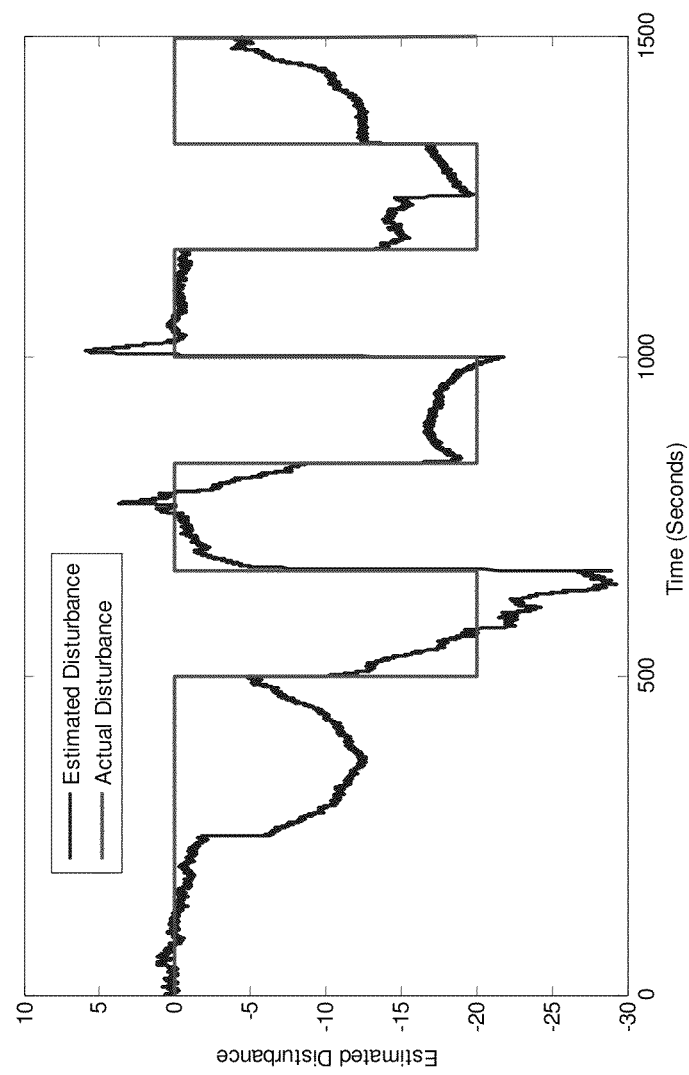
FIG. 34 illustrates the estimated disturbance from the discrete ESO compared to the actual disturbance for the varying parameters test.
Figure 35:
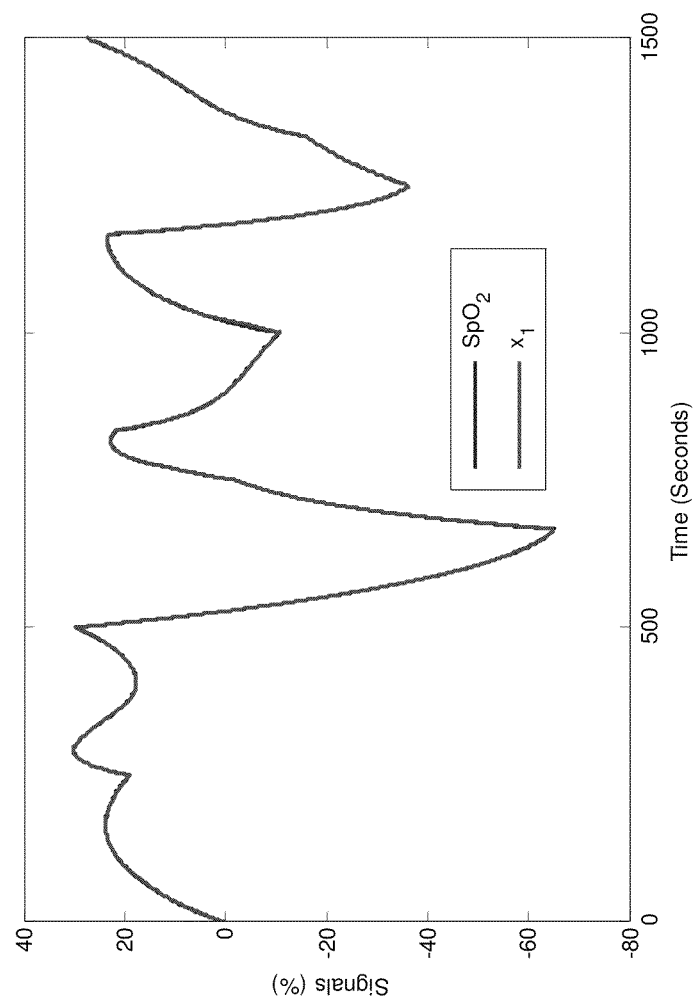
FIG. 35 illustrates the estimated $SpO_2$ from the discrete PE-EKF compared to the actual $SpO_2$ for the varying parameters test.
Figure 36:
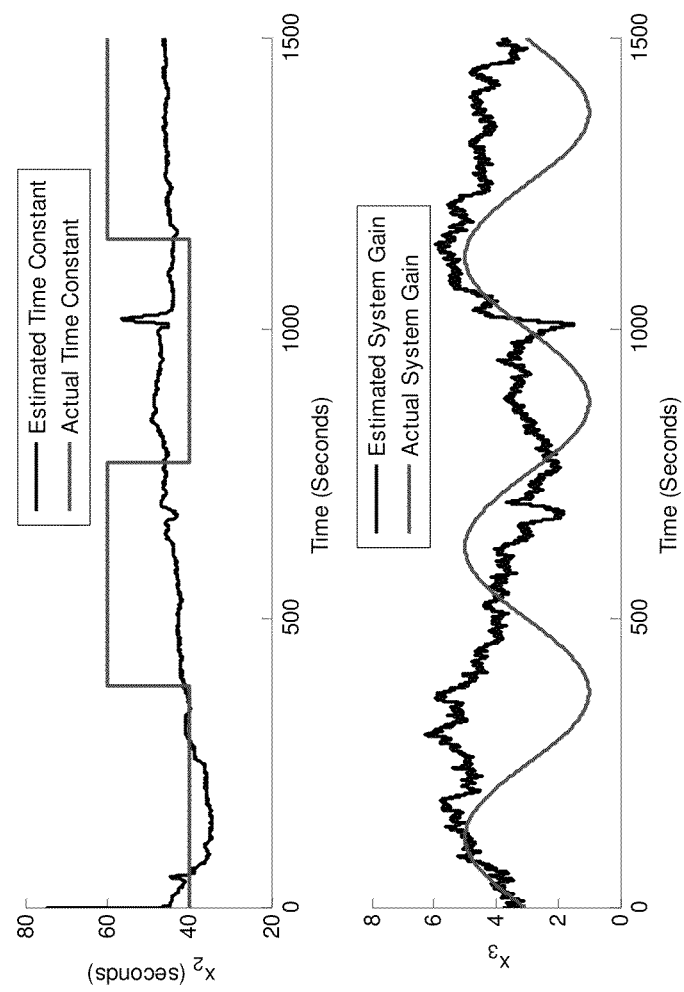
FIG. 36 illustrates the estimated time constant and system gain from the discrete PE-EKF compared to the actual parameters for the varying parameters test.
Figure 37:
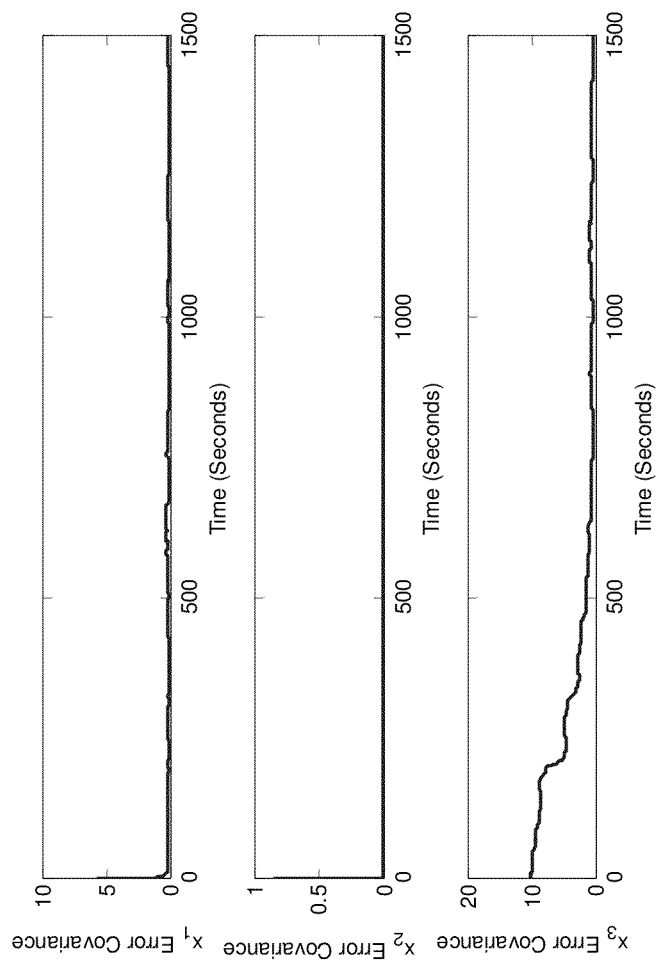
FIG. 37 illustrates the error covariance for each state in the discrete PE-EKF for the varying parameters test.
Figure 38:
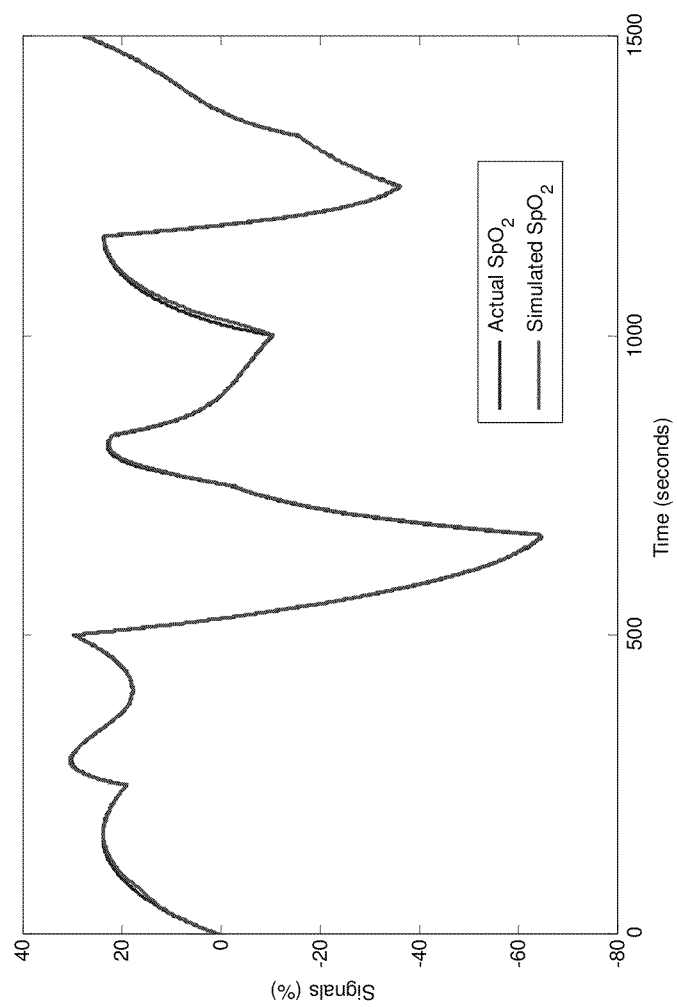
FIG. 38 illustrates the simulated $SpO_2$ using the estimated disturbance and system parameters compared to the $SpO_2$ for the varying parameters test.

The estimator system was then tested on a simulation with varying time constants and gain along with the unknown disturbance. The disturbance was a square wave oscillating at a 0.003 Hz frequency with an amplitude of 10 that started at 200 seconds. The input to the system was a square wave with a frequency of 0.002 Hz and an amplitude of 10. The system gain was a sine wave with a mean value of 3 oscillating at a frequency of 0.002 Hz and an amplitude of 2. The time constant was a square wave with a mean value of 50 oscillating at a frequency of 0.0013 Hz and an amplitude of 10. The FiO$_2$ from the model simulation that was used by the discrete ESO and the modified control that was used by the discrete PE-EKF can be seen in FIG. 32. The estimated SpO$_2$ from the ESO converged onto the SpO$_2$ data from the model simulation and can be seen in FIG. 33. The estimated disturbance from the discrete ESO was compared with the actual disturbance to the system can be seen in FIG. 34. The estimated SpO$_2$ from the discrete PE-EKF can be seen in FIG. 35. The estimated time constant and system gain was compared with the actual parameters can be seen in FIG. 36. The error covariance for each state of the discrete PE-EKF converged to small values can be seen in FIG. 37. The estimated disturbance and system parameters were used in the first-order system model to simulate the SpO$_2$ data and were compared to the actual SpO$_2$. The SpO$_2$ data from the model simulation matched the actual SpO$_2$ and can be seen in FIG. 38. The estimated system parameters did not match the actual time varying parameters, but the effects of error in the parameter estimates were included in the estimated disturbance signal. The SpO$_2$ data from the model simulation using the estimated values again matched the simulated data providing an accurate input-output model.

6. Testing of the Estimator System on One Hour Section of Data

Figure 39:
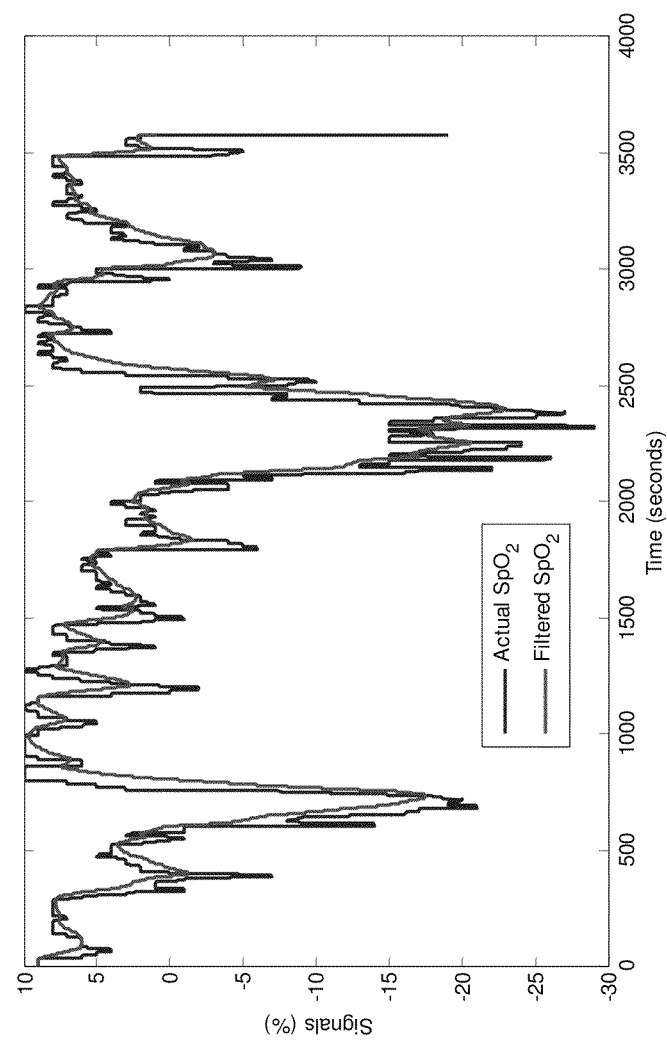
FIG. 39 illustrates the actual $SpO_2$ and the filtered $SpO_2$ after the discrete low pass filter.
Figure 40:
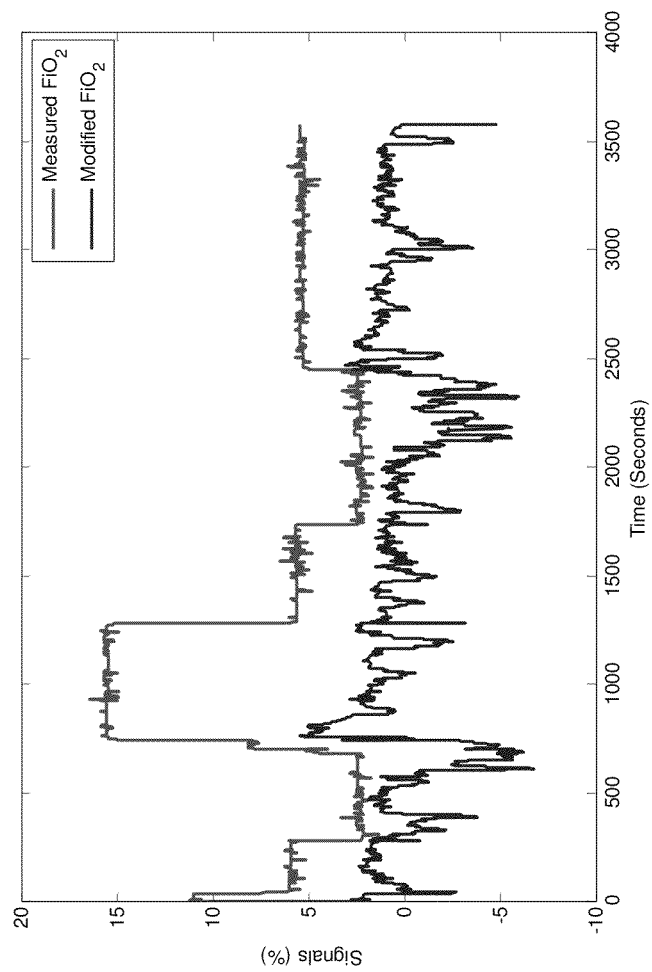
FIG. 40 illustrates the actual measured $FiO_2$ and the modified control sent to the PE-EKF.
Figure 41:
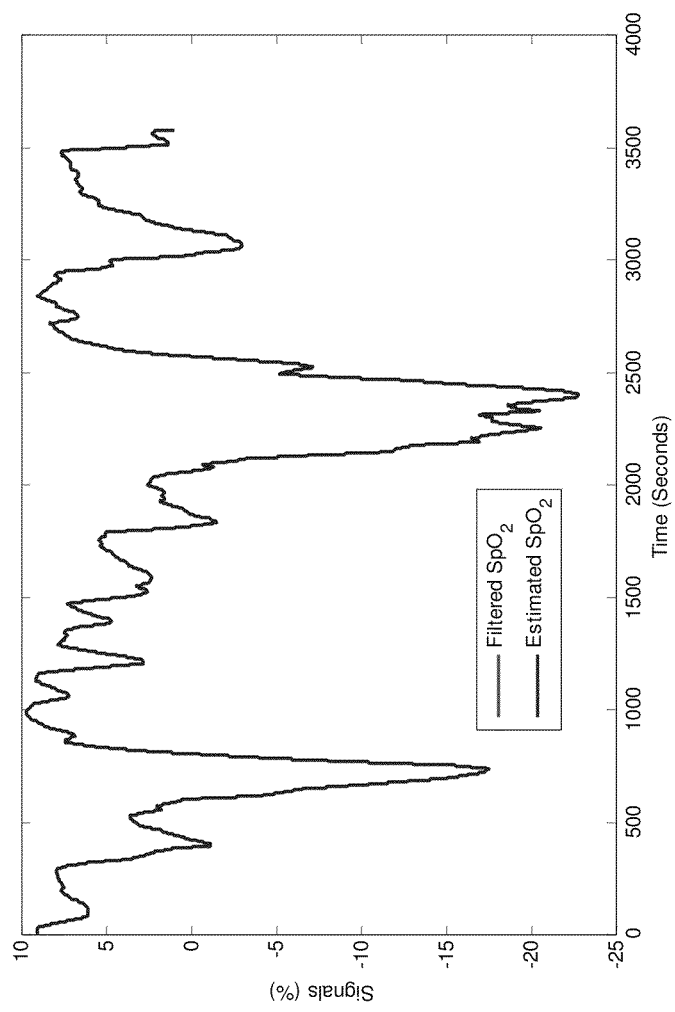
FIG. 41 illustrates the estimated $SpO_2$ from the ESO with the filtered $SpO_2$.
Figure 42:
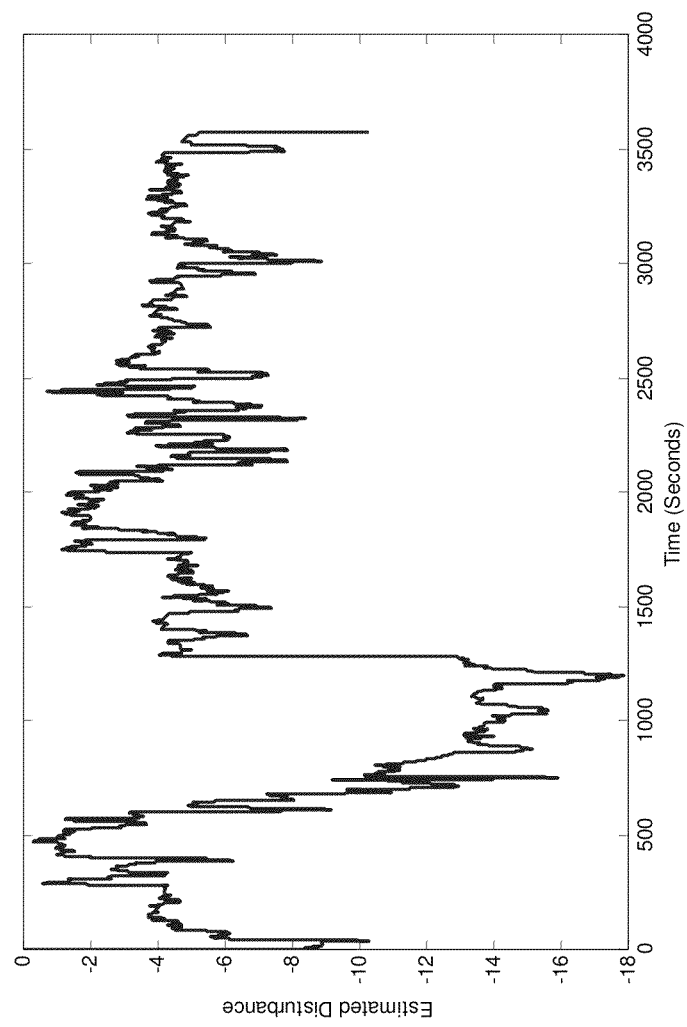
FIG. 42 illustrates the estimated disturbance from the ESO over one hour of patient data.
Figure 43:
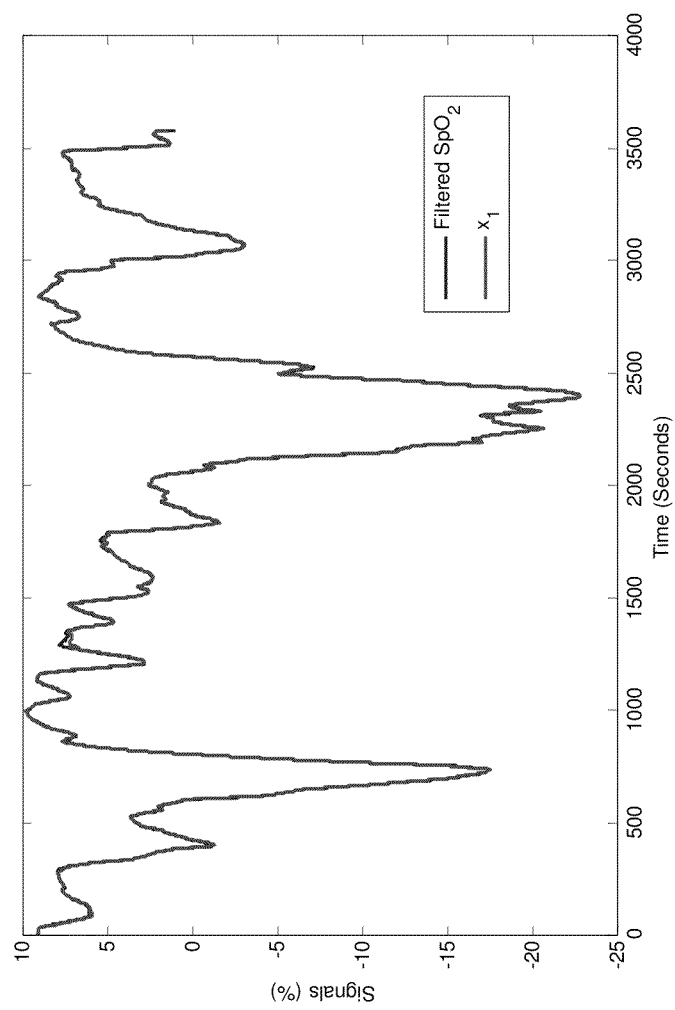
FIG. 43 illustrates the estimated $SpO_2$ from the PE-EKF with the filtered $SpO_2$.
Figure 44:
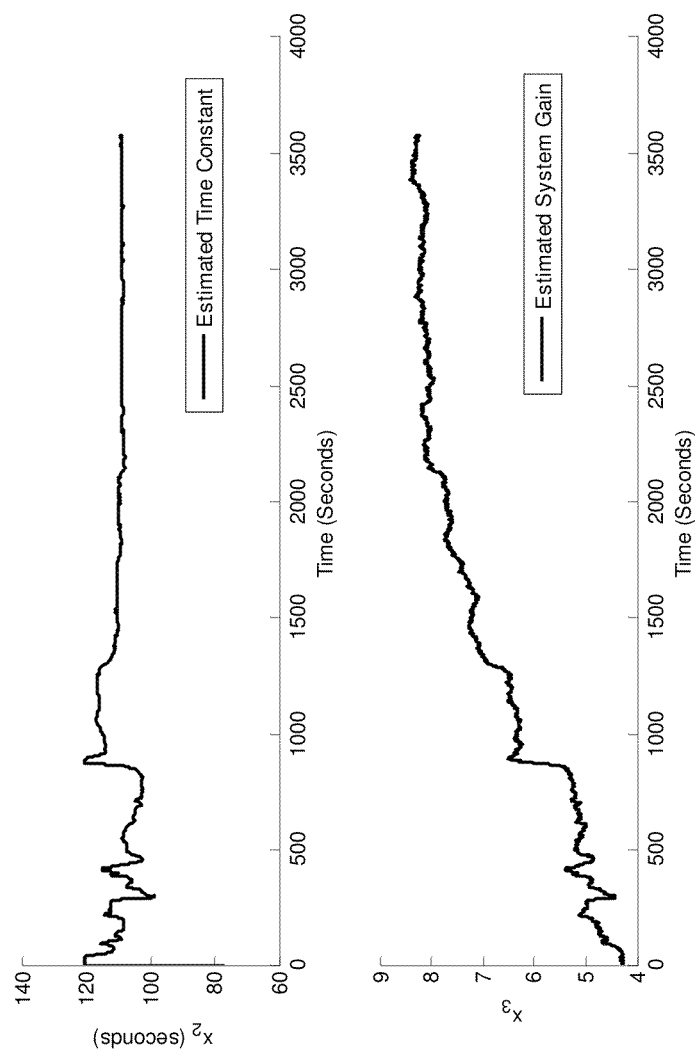
FIG. 44 illustrates the estimated time constant and system gain from the PE-EKF over one hour of patient data.
Figure 45:
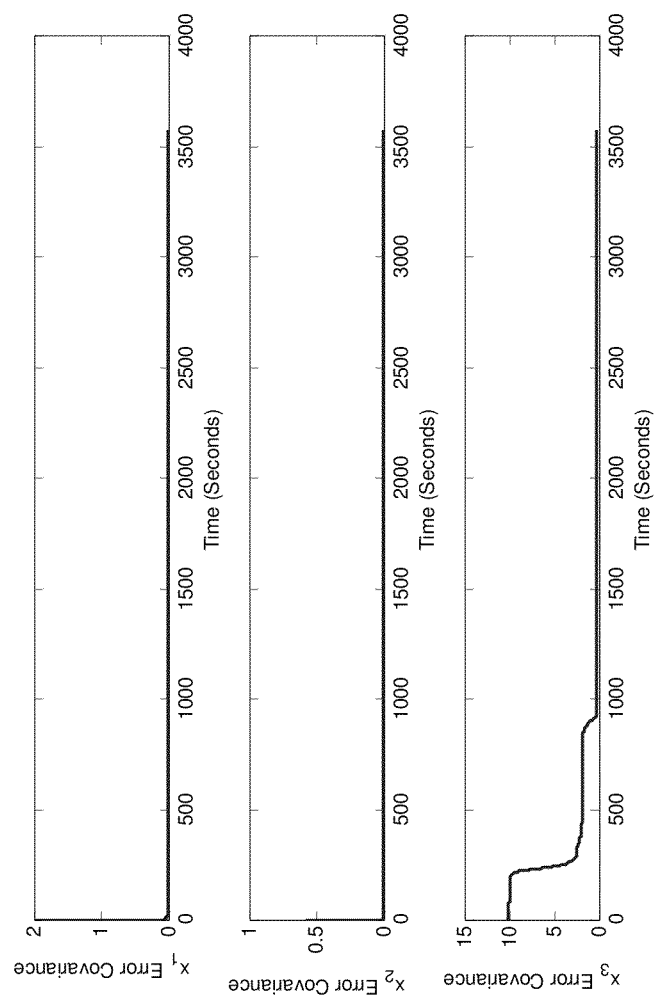
FIG. 45 illustrates the error covariance for each state of the PE-EKF over one hour of patient data.
Figure 46:
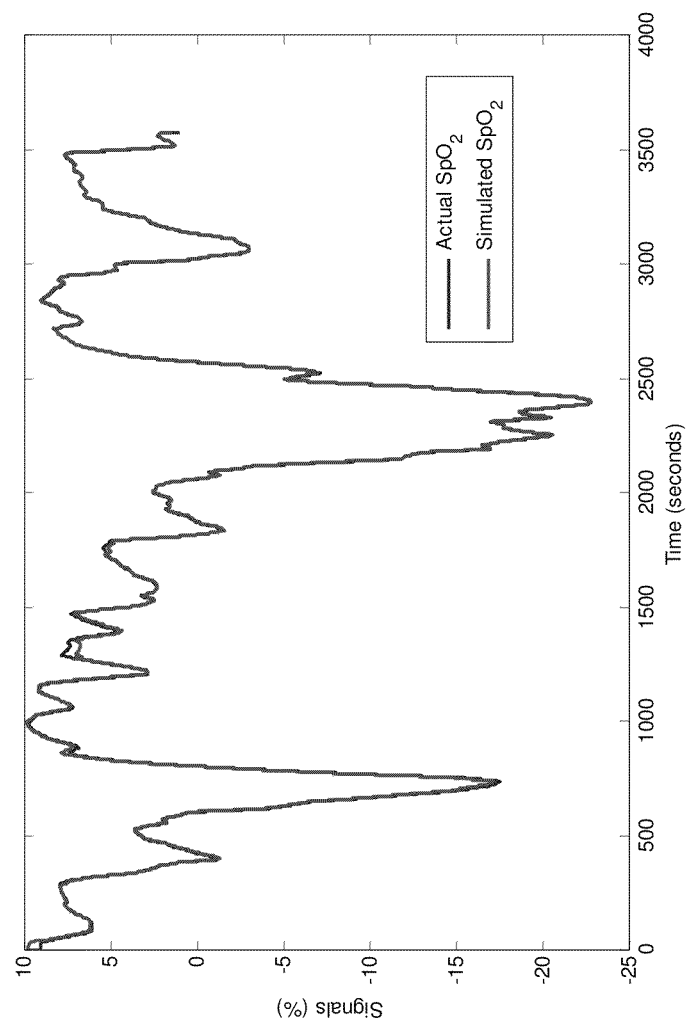
FIG. 46 illustrates the $SpO_2$ data from the model simulation with the discrete first-order system using the estimated disturbance and system parameters over one hour of patient data.

The estimator system was then tested on a one hour section of data. The patient data was resampled to a 0.1 second time step using linterp.m in Matlab. The measured SpO$_2$ was filtered using the discrete low pass filter from Section 3.6 and a graph showing the filtered and actual SpO$_2$ can be seen in FIG. 39. The measured FiO$_2$ control signal was modified by the disturbance for the PE-EKF and a graph of how the control signal was changed can be seen in FIG. 40. The ESO estimate of the SpO$_2$ converged onto the measured SpO$_2$ which can be seen in FIG. 41. The discrete ESO produced an estimated disturbance that corresponded to desaturation events observed in the patient data and a plot of the estimated disturbance can be seen in FIG. 42. The states of the PE-EKF converged to values within the found ranges of system parameters with low error covariance which can be seen in FIGS. 43, 44, 45, and 46. The SpO$_2$ data from the model simulation again accurately modeled the input-output relationship of the clinical FiO$_2$ and SpO$_2$ data.

7. Testing of the Estimator System Over Longer Sections of Data

Figure 47:
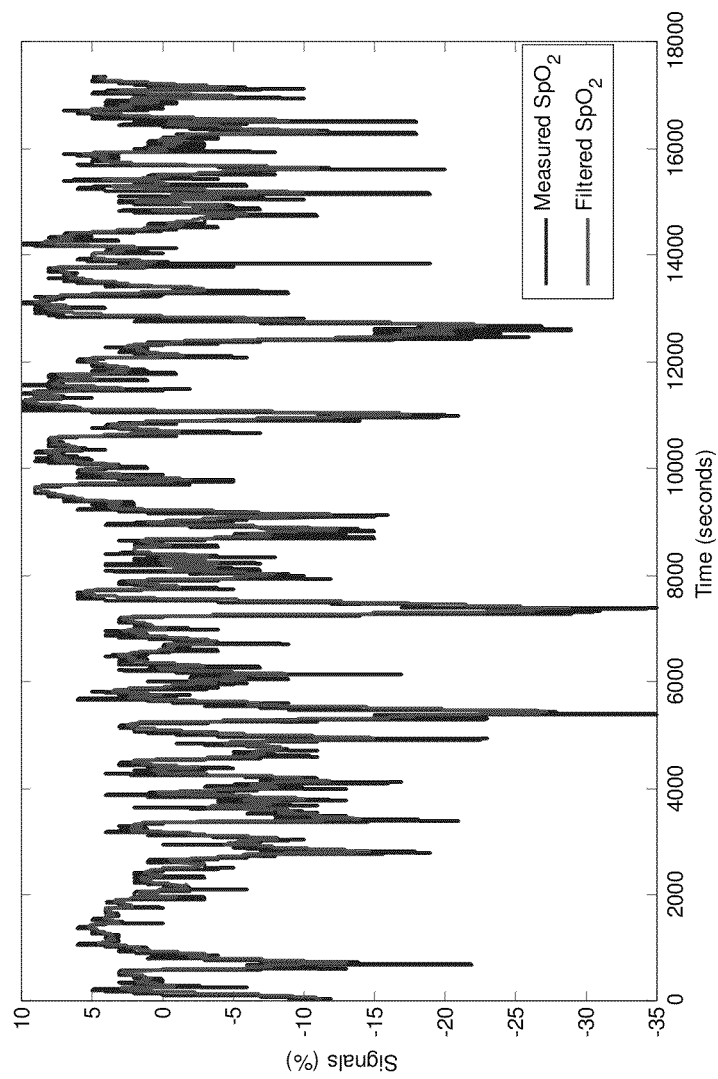
FIG. 47 illustrates the actual $SpO_2$ and filtered $SpO_2$ using the discrete low pass filter for five hours of patient data.
Figure 48:
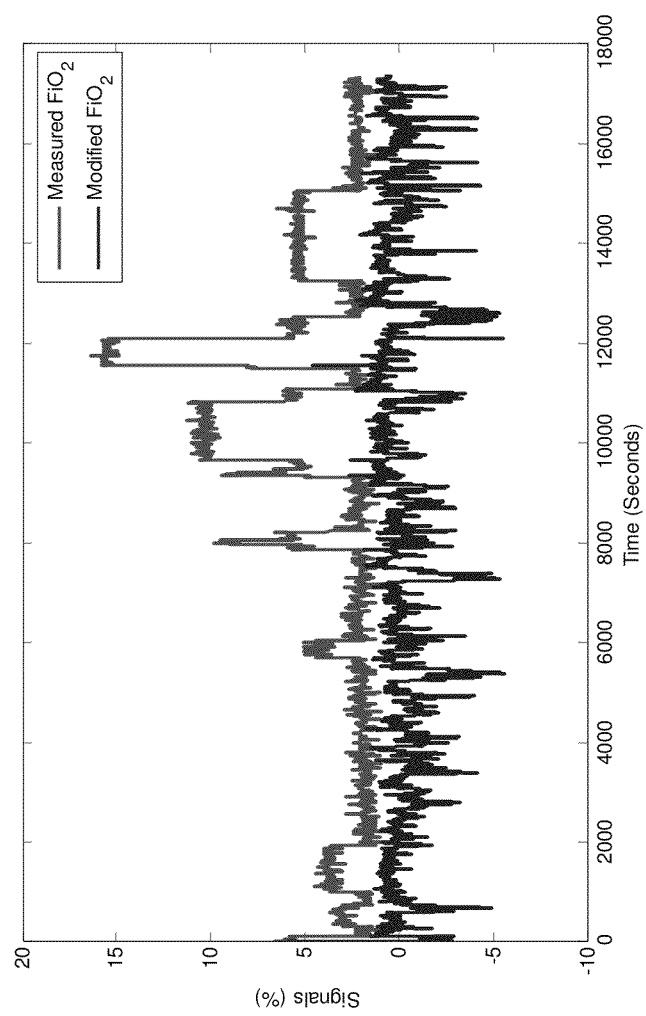
FIG. 48 illustrates the actual $FiO_2$ used in the discrete ESO and modified control used in the PE-EKF.
Figure 49:
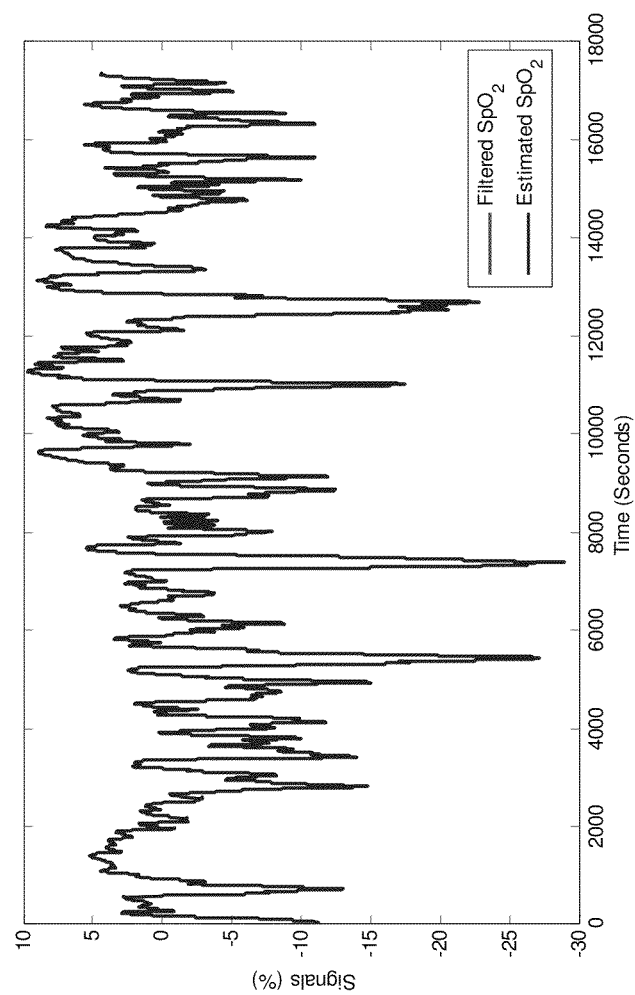
FIG. 49 illustrates the estimated $SpO_2$ from the discrete ESO with the filtered $SpO_2$ for five hours of patient data.
Figure 50:
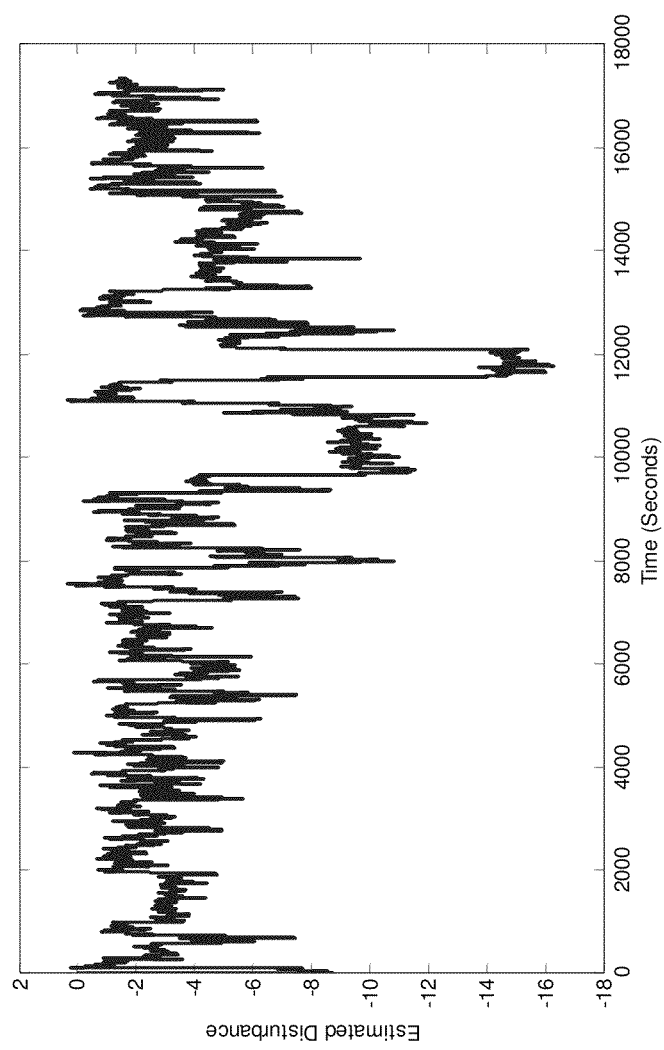
FIG. 50 illustrates the estimated disturbance from the ESO over five hours of patient data.
Figure 51:
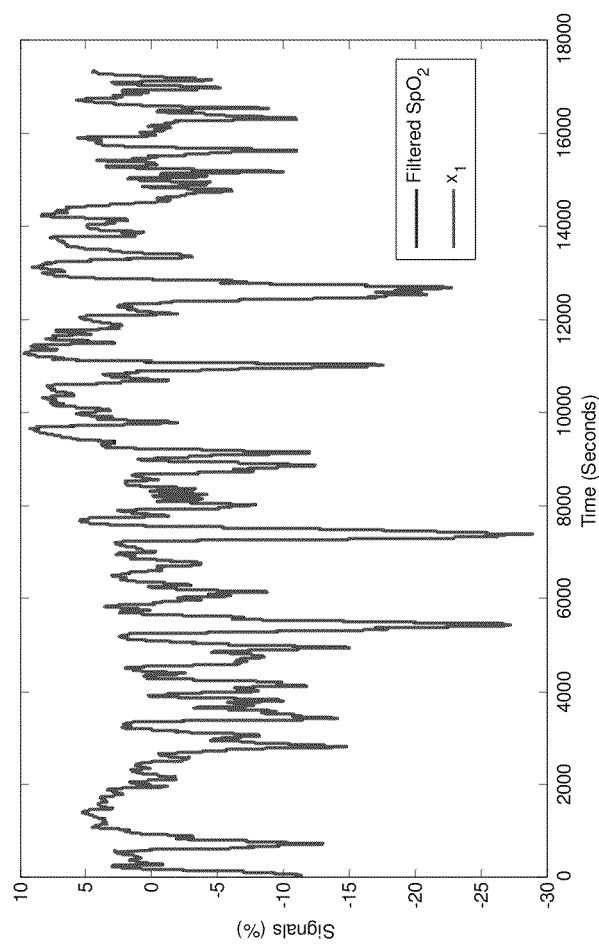
FIG. 51 illustrates the estimated $SpO_2$ from the PE-EKF with the filtered $SpO_2$ over five hours of patient data.
Figure 52:
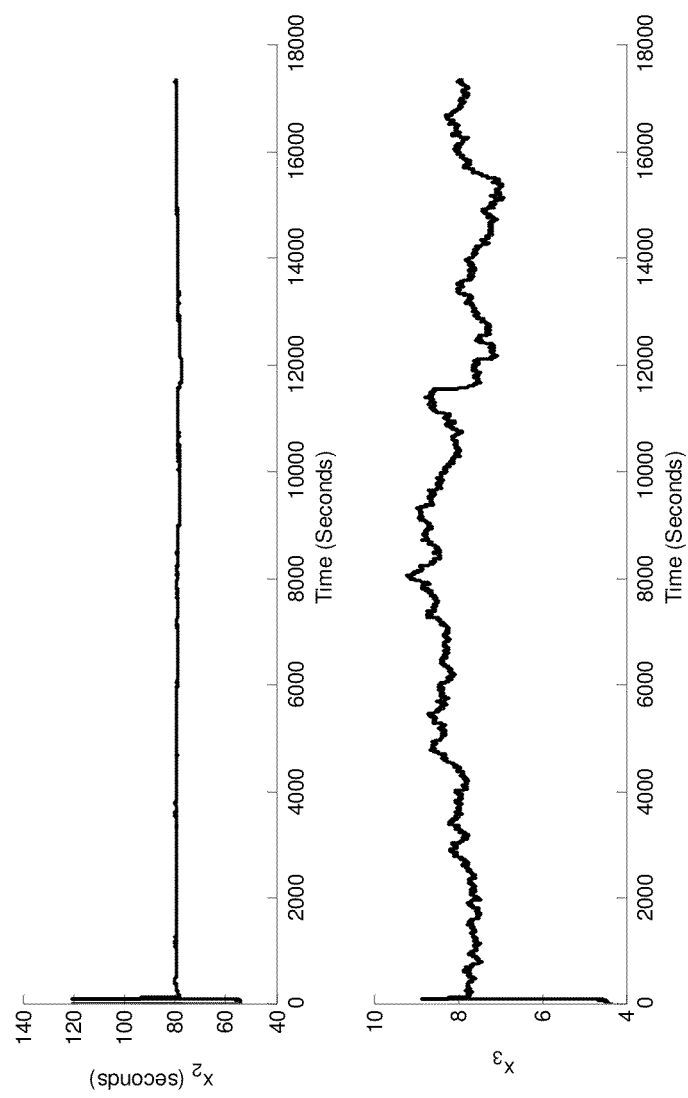
FIG. 52 illustrates the estimated time constant and gain for the PE-EKF over five hours of patient data.
Figure 53:
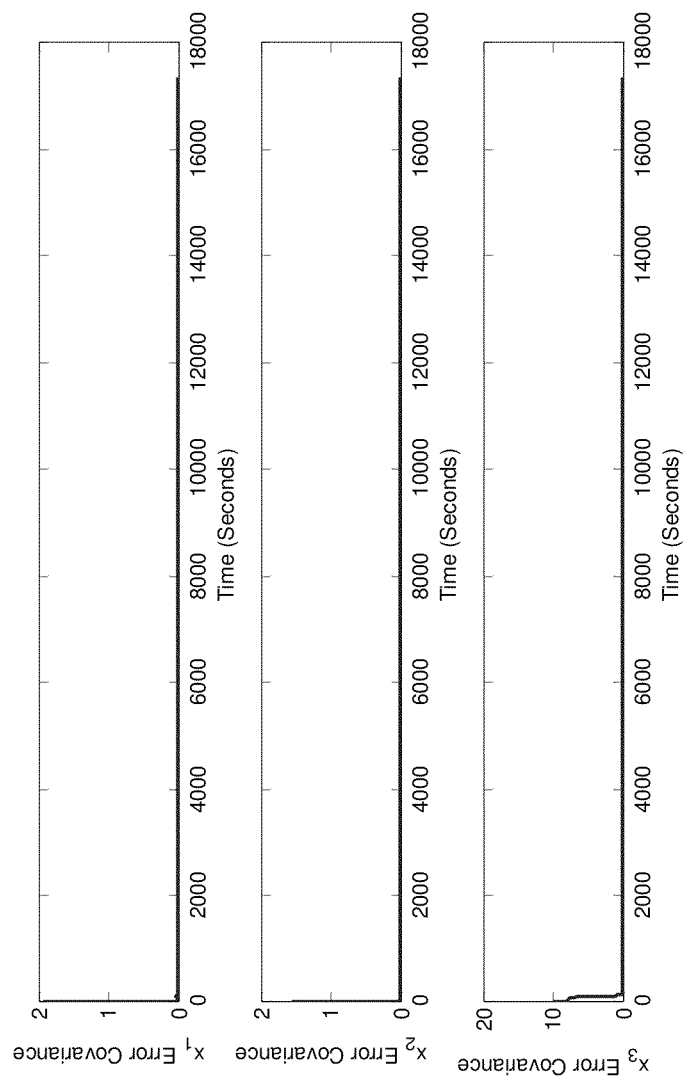
FIG. 53 illustrates the error covariance for each state of the PE-EKF over five hours of patient data.
Figure 54:
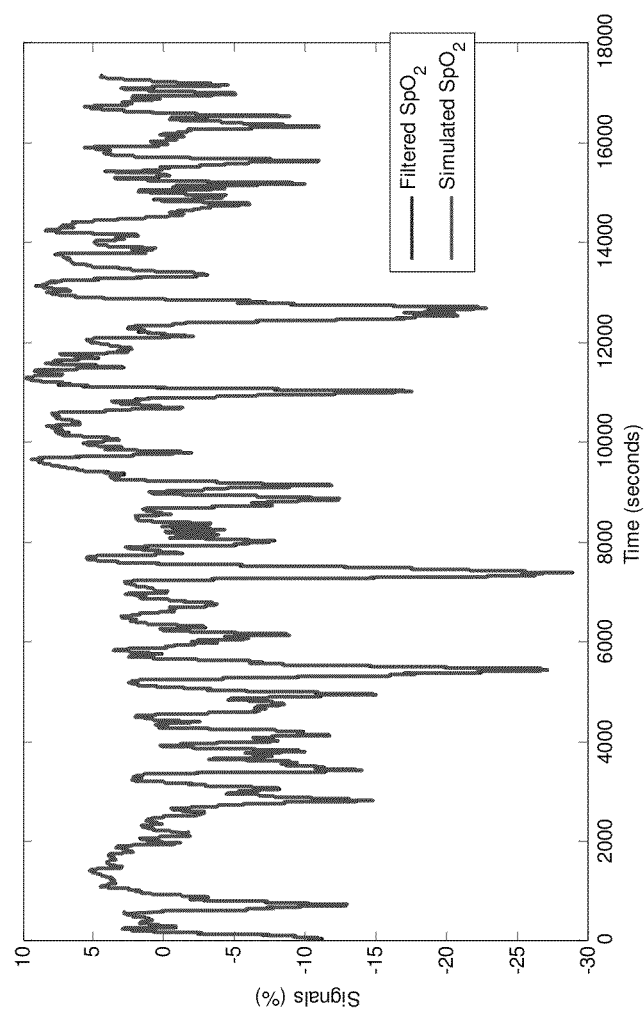
FIG. 54 illustrates the filtered $SpO_2$ compared to the $SpO_2$ data from the model simulation evaluated using the estimated disturbance and system parameters over five hours of patient data.

The estimator system was then tested for convergence over longer sections of data. A five hour section of patient data was chosen and the estimation system was evaluated. The initial conditions for the ESO and PE-EKF were the same as previous tests. The patient data was resampled at 0.1 seconds. The measured SpO$_2$ from patient data was first filtered using the discrete low pass filter and the measured and filtered SpO$_2$ can be seen in FIG. 47. The actual FiO$_2$ that was used in the ESO and the modified control that was used in the PE-EKF can be seen in FIG. 48. The estimated SpO$_2$ from the ESO converged onto the filtered SpO$_2$ and can be seen in FIG. 49. The estimated disturbance from the ESO can be seen in FIG. 50. The estimated SpO$_2$ from the PE-EKF converged onto the filtered SpO$_2$ and can be seen in FIG. 51. The estimated time constant and system gain can be seen in FIG. 52. The error covariance for each state of the PE-EKF converged to small values and can be seen in FIG. 53. The estimated system parameters and disturbance were then used to simulate the discrete first-order system which matched the filtered SpO$_2$ showing that the estimation system provided an accurate representation of the input-output relationship which can be seen by the low error covariance in FIG. 54.

One skilled in the art would readily appreciate that the system and methods described herein are representative of exemplary embodiments, and not intended as limitations on the scope of the invention. It will be readily apparent to one skilled in the art that varying substitutions and modifications may be made to the present disclosure disclosed herein without departing from the scope and spirit of the invention.

The present disclosure illustratively described herein suitably may be practiced in the absence of any element or elements, limitation or limitations that are not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

The invention claimed is:

1. An automatic system for controlling $SpO_2$ in the blood of a patient, the system comprising:
   a. an adaptive microcontroller;
   b. a device that controls the variable adjustment of $FiO_2$ delivered to the patient through a blend valve; and
   c. a monitoring device,
wherein the adaptive microcontroller receives signals from the monitoring device pertaining to clinical measurements of the patient, processes the signals with dynamic adaptability through an algorithm and sends corresponding signals to the device that controls the variable adjustment of $FiO_2$ delivered to the patient depending on the signals received by the microcontroller from the monitoring device, wherein the microcontroller is in direct communication with the monitoring device through an inbound/outbound electronic communication means selected from the group consisting of a serial port adapter, USB adapter, firewire, Ethernet cable, wireless communication, and combinations thereof, and wherein the algorithm comprises an estimation system consisting of a discrete parameter-estimating extended Kalman filter and extended state observer.

2. The system of claim 1, wherein the device that controls the variable adjustment of $FiO_2$ is comprised of a servo motor.

3. The system of claim 2, wherein the servo motor is in direct communication with the microcontroller through an inbound/outbound electronic communication means selected from the group consisting of a serial port adapter, USB adapter, firewire, Ethernet cable, wireless communication, and combinations thereof.

4. The system of claim 3, wherein the servo motor automatically adjusts the blend valve in response to a signal sent to the motor by the microcontroller.

5. The system of claim 1, wherein the monitoring device is selected from the group consisting of a bedside monitor interface, pulse oximeter, oxygen analyzer, and combinations thereof.

6. The system of claim 1, wherein the system further comprises a device to control variable adjustment of flow of gas to the patient through a flow valve.

7. The system of claim 6, wherein the device to control variable adjustment of oxygen is comprised of a servo motor.

8. The system of claim 7, wherein the servo motor automatically adjusts the oxygen flow valve in response to a signal sent to the servo motor by the microcontroller.

9. The system of claim 1, wherein the device further comprises a device to stimulate the patient.

10. The system of claim 9, wherein the device to stimulate the patient comprises a motor, wherein the motor is a vibration motor.

11. The system of claim 9 wherein the device to stimulate the patient is attached to an extremity of the patient.

12. The system of claim 9, wherein the device to stimulate the patient is in direct communication with the microcontroller through an inbound/outbound electronic communication means selected from the group consisting of a serial port adapter, ribbon cable module, USB adapter, firewire, Ethernet cable, wireless communication, and combinations thereof.

13. An automatic system for controlling $SpO_2$ in the blood of a patient, the system comprising:
   a. an adaptive microcontroller;
   b. a device to control variable adjustment of $FiO_2$ delivered to the patient;
   c. a device to control variable adjustment of flow of gas delivered to the patient;
   d. a device to stimulate the patient; and
   e. a monitoring device,
wherein the adaptive microcontroller receives signals from the monitoring device pertaining to clinical measurements of the patient, processes the signals with dynamic adaptability through an algorithm and sends corresponding signals to the devices controlling the variable adjustment of $FiO_2$ and flow of gas to the patient depending on the signal received by the microcontroller from the monitoring device, wherein the microcontroller is in direct communication with the monitoring device through an inbound/outbound electronic communication means selected from the group consisting of a serial port adapter, USB adapter, firewire, Ethernet cable, wireless communication, and combinations thereof, and wherein the algorithm comprises an estimation system consisting of a discrete parameter-estimating extended Kalman filter and extended state observer.

14. A method of using the automatic system of claim 1, the method comprising the steps of:
   a. monitoring the patient through the monitoring device;
   b. sensing the $FiO_2$ of the patient at any given time through angular position of the blend valve;
   c. determining through algorithm the necessary adjustment to the blend valve in order to provide optimum $FiO_2$ output as required by the patient; and
   d. automatically adjusting the blend valve.

15. The method of claim 14, wherein the method further comprises sensing the flow of gas to the patient at any given time through position of a flow valve.

16. The method of claim 15, wherein the method further comprises determining through algorithm the necessary adjustment to the flow valve as required by the patient.

17. The method of claim 16, wherein the method further comprises automatically adjusting the flow valve.

* * * * *